United States Patent
Bell et al.

(10) Patent No.: US 6,211,107 B1
(45) Date of Patent: Apr. 3, 2001

(54) PROCESS FOR EXPOXIDIZING PROCHIRAL OLEFINS AND A CATALYST THEREFOR AND INTERMEDIATES FOR MAKING THE CATALYST

(75) Inventors: David Bell, Hertford; Frances Finney, Sawbridgeworth; Robin Patrick Attrill, Harlow; David Miller, Bishops Stortford; Gillian Turner, Harlow, all of (GB)

(73) Assignee: SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/141,131

(22) Filed: Aug. 27, 1998

Related U.S. Application Data

(62) Division of application No. 08/687,420, filed as application No. PCT/EP95/00370 on Feb. 1, 1995, now Pat. No. 5,916,975.

(51) Int. Cl.[7] .............................. B01J 21/00; B01J 21/02; B01J 21/10; B01J 23/02; B01J 23/04
(52) U.S. Cl. ..................... 502/150; 502/155; 502/156; 502/162; 502/167; 526/90; 526/161; 526/172
(58) Field of Search ..................... 502/155, 156; 525/270, 332.8, 332.9, 333.1, 333.2; 552/524, 525, 531, 533; 556/45; 568/700, 704, 705, 706, 707, 716

(56) References Cited

U.S. PATENT DOCUMENTS

| | | | |
|---|---|---|---|
| 3,787,501 | 1/1974 | Kallianos et al. | 260/592 |
| 4,861,904 | 8/1989 | Sugie et al. | 556/32 |
| 5,266,565 | 11/1993 | LaCoste et al. | 514/114 |
| 5,281,578 | 1/1994 | Bradley et al. | 514/6 |
| 5,916,975 | * 6/1999 | Bell et al. | 525/270 |

OTHER PUBLICATIONS

Jacobsen et al. (J. Am. Chem. Soc. 1991, 113, 7063–7064 . . . "Highly Enantioselective Epoxidation Catalysts. . .") Aug. 1991.*

Jacobsen et al. (J. Am. Chem. Soc., 1991, 6703–6704 . . . "Electronic Tuning of Asymmetric Catalysts") Aug. 1991.*

* cited by examiner

*Primary Examiner*—Mark L. Bell
*Assistant Examiner*—Michael J. DiVerdi
(74) *Attorney, Agent, or Firm*—Mary E. McCarthy; Stephen Venetianer; Charles M. Kinzig

(57) ABSTRACT

This invention relates to the catalyst (III) and intermediates for its preparation in which M is a transition metal ion; A is a counter-ion if required; B, B', and E and E' are independently selected from the group consisting of hydrogen aryl, $C_{1-6}$alkyl, silyl or aryl-$C_{1-6}$ alkyl in which any aryl or alkyl moiety is optionally substituted or B' and B or E' and E together form a $C_{2-6}$ polymethylene link; with the proviso that only one of the carbons marked with an asterisk if a chiral center; $R_1$, $R_2$, $R_3$, $R_4$, $R_5$, $R_6$, $R_7$, $R_8$, $R_9$ and $R_{10}$ are independently hydrogen, alkyl or alkoxy

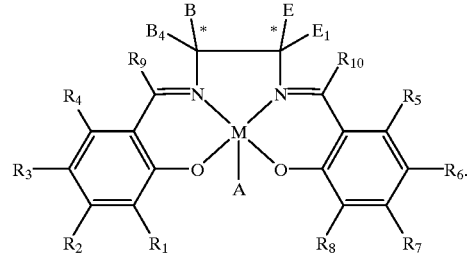

(III)

6 Claims, No Drawings

PROCESS FOR EXPOXIDIZING PROCHIRAL OLEFINS AND A CATALYST THEREFOR AND INTERMEDIATES FOR MAKING THE CATALYST

This is a divisional of application Ser. No. 08/687,420, filed Aug. 5, 1996, now U.S. Pat. No. 5,916,975, which is a 371 of International Application No. PCT/EP95/00370, filed Feb. 1, 1995.

This invention relates to a novel process for preparing epoxides from olefins and in particular chirally enriched epoxides, certain novel catalysts used in such process and compounds associated with process.

WO 91/14694 described certain catalysts of the following formula (I):

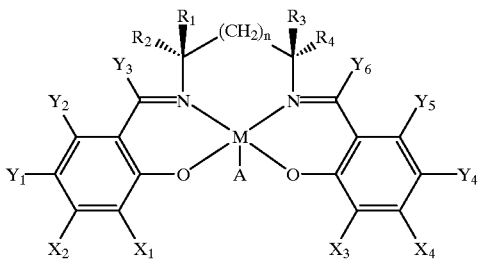

(I)

in which

M is a transition metal ion, A, is an anion, and n is either 0, 1 or 2. At least one of $X_1$ or $X_2$ is selected from the group consisting of silyls, aryls, secondary alkyls and tertiary alkyls; and at least one of $X_3$ or $X_4$ is selected from the same group. $Y_1, Y_2, Y_3, Y_4, Y_5$ and $Y_6$ are independently selected from the group consisting of hydrogen, halides, alkyls, aryl groups, silyl groups, and alkyl groups bearing heteroatoms such as alkoxy and halide, Also, at least one of $R_1, R_2, R_3$ and $R_4$ is selected from a first group consisting of H, $CH_3$, $C_2H_5$ and primary alkyls. Furthermore, if $R_1$ is selected from said first group, then $R_2$ and $R_3$ are selected from a second group consisting of aryl groups, heteroatom-bearing aromatic groups, secondary alkyls and tertiary alkyls. If $R_2$ is selected from said first group, then $R_1$ and $R_4$ are selected from said second group. If $R_3$ is selected from said first group, and $R_1$ and $R_4$ are selected from said second group. If $R_4$ is selected from said first group, then $R_2$ and $R_3$ are selected from said second group. Such catalysts are described as being useful in enantioselectively epoxidising a prochiral olefin.

In addition WO 91/14694 described certain catalysts of the formula shown below, herein referred to as formula (IA):

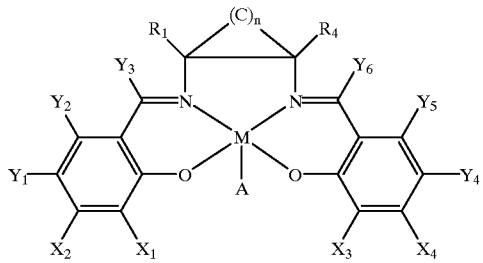

(IA)

where M is defined as a transition metal ion and A is an anion; where n is either, 3,4,5 or 6; where at least one of $X_1$ or $X_2$ is selected from the group consisting of aryls, primary alkyls, secondary alkyls, tertiary alkyls, and hetero atoms; where at least one of $X_3$ or $X_4$ is selected from the group consisting of aryls, primary alkyls, secondary alkyls, tertiary alkyls, and hetero atoms; where at least one of $Y_1$ or $Y_2$ is selected from the group consisting of aryls, primary alkyls, secondary alkyls, tertiary alkyls, and hetero atoms; where at least one of $Y_4$ or $Y_5$ is selected from the group consisting of aryls, primary alkyls, secondary alkyls, tertiary alkyls, and hetero atoms; where $Y_3$ and $Y_6$ are independently selected from the group consisting of hydrogen and primary alkyl groups; where $R_1$ and $R_4$ are trans to each other and at least one of $R_1$ and $R_4$ is selected from the group consisting of primary alkyls and hydrogen; and where the carbons in the $(C)_n$ portion have substituents selected for the group consisting of hydrogen, alkyl, aryl, and heteratoms.

Such catalysts are described as being useful in enantioselectively epoxidising a prochiral olefin. These catalysts belong to the class of catalysts known in the art as 'salen catalysts.'

Co-pending International Patent Application Number PCT/GB93/01666 (now International Patent Application, Publication Number WO 94/03271) also discloses a series of salen catalysts, structurally distinct from the catalysts for formula (I) and having the general formula (II):

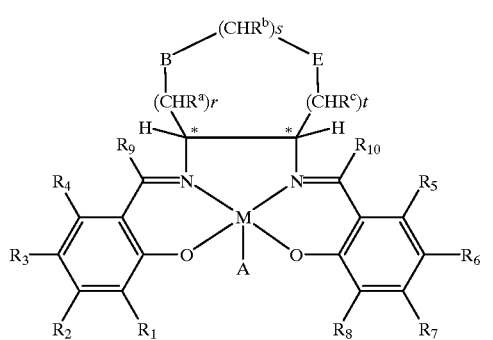

(II)

in which M is a transition metal ion:
A is a counter-ion if required;
r, s and t are independently 0 to 3 such that r+s+t is in the range of 1 to 3;
$R^a, R^b, R^c$ are each independently hydrogen or $CH_2OR'$ where R' is hydrogen or an organic group;
B and E are independently oxygen, $CH_2$, $NR^d$ in which $R^d$ is alkyl, hydrogen, alkylcarbonyl, or alkylcarbonyl or $SO_n$ where n is 0 or an integer 1 or 2, with the proviso that B and E are not simultaneously $CH_2$ and that when B is oxygen, $NR^d$ or $SO_n$, then r cannot be 0, and when E is oxygen, $NR^d$ or $SO_n$, then t cannot be 0;
$R_1, R_2, R_3, R_4, R_5, R_6, R_7, R_8, R_9$ and $R_{10}$ are independently hydrogen, alkyl or alkoxy.

The compounds of formula (II) also catalyse the enantioselective expoxidiation of certain prochiral olefins.

It has been suggested in the art that the use of compounds such as pyridine oxide and 2-methyl imidazole in combination with certain chiral (salen) manganese (III) complex catalysts improves the chemical yield such reactions (Syn. Lett. April 1991, 265–266), although the effect upon the enantioselectivity of the catalysed reactions is currently not clear (Tetrahedron Vol. 50, No 15 p. 4323–4334, 1994). In this context pyridine oxide and 2-methyl imidazole are referred to as 'donor ligands' as they are considered to donor-bond to the metallic ion of the salen catalyst.

One particular problem associated with the use of such donor ligands is the complete removal of the donor ligand from the final epoxide product, especially in large scale reactions and most especially when two phase reaction systems are used.

It has now been discovered that one particular compound, isoquinoline N-oxide, previously unreported as a donor ligand, is particularly efficient as a donor ligand in that it advantageously enhances catalyst turnover and in addition it possesses very good solubility characteristics for use as a donor ligand, enabling it to be used in the metal salen complex catalysed epoxidation reactions and subsequently to be readily removed from the epoxide products of the reaction. It has also been discovered that a particular group of salen catalysts are especially suited to use with donor ligands in that the presence of the donor ligands consistently produces not only an increase in reaction rate but also an increase in the enantioselective specificity of the epoxidation reactions.

In addition a further series of salen catalysts which are structurally distinct from those of formulae, (I), (IA) and (II) has now been prepared which surprisingly are also able to catalyse the enantioselective expoxidiation of certain prochiral olefins.

Accordingly, in a first aspect, the invention provides a process for enantioselectively epoxidising a prochiral olefin, which process comprises reacting the prochiral olefin with a source of oxygen in the presence of a salen catalyst and a source of an electron donating ligand, characterised in that the donor ligand is isoquinoline N-oxide or a compound having donor ligand activity and having substantially the same solubility characteristics as isoquinoline N-oxide.

A suitable salen catalyst is a compound of formula (I), (IA), (II) or a compound of formula (III) (which compound of formula (III) is defined hereinafter).

The invention also provides isoquinoline N-oxide or a compound having donor ligand activity and having substantially the same solubility characteristics as isoquinoline N-oxide, for use as a donor ligand.

In a further aspect the invention provides a process for enantioselectively epoxidising a prochiral olefin, which process comprises reacting the prochiral olefin with a source of oxygen in the presence of a salen catalyst and a source of an electron donating ligand, characterised in that the salen catalyst is a compound of formula (II).

A source of an electron donating ligand is suitably provided by a compound which is capable of forming a donor bond with the transition metal M of the said salen catalyst, such that in use the rate of the epoxidation reaction is increased and the enantioselective specificity of the resulting product may also be increased.

A source of electron donating ligand is suitably provided by a compound which is capable of forming a donor bond with the transition metal M of the salen catalyst such that in use the enantioselective specificity of the compound of formula (I) is increased.

A suitable source of an electron donating ligand may be selected from the list consisting of pyridine N-oxide, 2-methyl pyridine N-oxide, 4-methyl pyridine N-oxide, 4-phenyl pyridine N-oxide or isoquinoline N-oxide, especially isoquinoline N-oxide.

In the compounds of formula (I) and (IA);

Preferred values for M, A, n, $X_1$, $X_2$, $X_3$, $X_4$, $Y_1$, $Y_2$, $Y_3$, $Y_4$, $Y_5$, $Y_6$, $R_1$, $R_2$, $R_3$ and $R_4$ are as defined in WO 91/14694.

Suitable catalysts are those of formula (IA) as defined above.

A preferred sub-group of catalysts are those of formula (IB) as defined below:

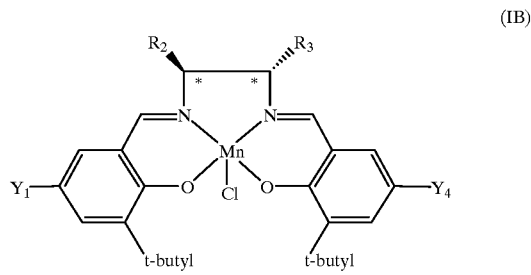

(IB)

in which $Y_1$ and $Y_4$ are the same and are selected from the group consisting of methyl t-butyl or methoxy and $R_2$ and $R_3$ are either both phenyl or together with the carbon atoms to which they are attached form a hexyl ring.

Most preferably, in catalysts of formula (IB), $Y_1$ and $Y_4$ are both t-butyl and $R_2$ and $R_3$ together with the carbon atoms to which they are attached form a hexyl ring.

In the compounds of formula (II):

The suitable, favoured and preferred values of the variables A, B, E, $R^a$, $R^b$, $R^c$, $R^d$, R' $R_1$, $R_2$, $R_3$, $R_4$, $R_5$, $R_6$, $R_7$, $R_8$, $R_9$, $R_{10}$, n, r, s and t are as described in WO 94/03271 unless otherwise stated herein.

Suitable organic groups R' include alkyl, alkylcarbonyl, arylcarbonyl or aryl derivatives.

Particular examples of R' include substituted alkyl groups.

One example of R' is a triphenylmethyl group.

Preferably s and t are zero, r is 1 and $R^a$ is hydrogen, B is oxygen and E is $CH_2$; or r, s and t are 1, $R^a$, $R^b$ and $R^c$ are hydrogen and B and E are both oxygen; or s is zero, r and t are both 1, $R^a$ is hydrogen or triphenylmethyloxymethylene and $R^c$ is hydrogen. B is oxygen and E is —$CH_2$-; or r and t are both 1, s is zero, $R^a$ and $R^c$ are hydrogen, B is $NR^d$ where $R^d$ is phenyl carbonyl and E is $CH_2$.

Suitably, $R_2$, $R_4$, $R_5$ and $R_7$ each independently represent hydrogen.

Suitably $R_1$, $R_3$, $R_6$ and $R_8$ each independently represent $C_{1-6}$ alkyl.

Favourably $R_1$ and $R_8$ represent branched alkyl groups such as tertiary alkyl groups.

$R_3$ and $R_6$ also advantageously represent branched alkyl groups.

One preferred example for each of $R_1$ and $R_8$ is tertiary butyl.

Particular examples of $R_3$ and $R_6$ are tertiary butyl and methyl.

Examples of $R_2$, $R_4$, $R_5$ and $R_7$ are hydrogen.

Examples of the compounds of formula (II) include those exemplified in WO 94/03271 and particularly include those compounds referred to herein.

As stated above a further aspect of the invention is the discovery of a novel series of salen catalysts:

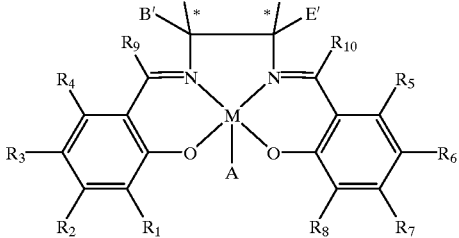
(III)

in which M is a transition metal ion;

A is a counter-ion if required;

B, B', E and E' are independently selected form the group consisting of hydrogen aryl, $C_{1-6}$ alkyl, silyl or aryl $-C_{1-6}$ alkyl in which any aryl or alkyl moiety is optionally substituted or B' and B or E' and E together form a $C_{2-6}$ polymethylene link; with the proviso that only one of the carbons marked with an asterisk is a chiral centre; $R_1$, $R_2$, $R_3$, $R_4$, $R_5$, $R_6$, $R_7$, $R_8$, $R_9$ and $R_{10}$ are independently hydrogen, alkyl or alkoxy.

Suitably, a compound according to formula (III), wherein $R_2$, $R_4$, $R_5$ and $R_7$ each independently represent hydrogen and $R_1$, $R_3$, $R_6$ and $R_8$ each independently represent $C_{1-6}$ alkyl.

Suitably, a compound according to formula (III) wherein one of B and E is phenyl, methyl or isopropyl and the other is hydrogen.

It should be appreciated that in some cases for example when M is Mn (II), a counter-ion is not required.

Suitable counter-ions, A, include those anions mentioned in WO91/14694 and WO 94/03271.

Preferably, A is chloride.

In the process of the invention:

Suitable prochiral olefins include compounds which comprise the following groups as part of their structure, cyclohexene, 5,6-dihydro-2H-pyran, 1,2,5,6-tetrahydropyridine, 1,2,3,4-tetrahydropyridine and 5,6-dihydro-2H-thiopyran.

Favoured prochiral olefins include those compounds which comprise the following groups as part of their structure form: 1,2-dihydronaphthalene, 2H-chromene, 1,2-dihydroquinoline, 1,2-dihydroisoquinoline and 2H-thiochromene. Such compounds are well known in the potassium channel activator field.

Preferred prochiral olefins include those mentioned in EP-A-0 376 524, such as the compounds of formula (XIV) therein, and in particular 2,2-dimethyl-6-pentafluoroethyl-2H-1-benzopyran.

Preferred prochiral olefins include 6-acetyl-2,2-dimethyl-2H-1-benzopyran.

Suitable oxygen sources include oxidising agents such as sodium hypochlorite.

The epoxidation reaction may be carried out using any suitable procedure wherein the prochiral olefin, the source of oxygen, the compound of formula (I) and the source of the electron donating ligand are allowed to react to provide the required epoxide.

Suitably, the reaction is carried out in a two phase system, especially when the source of oxygen and/or one of the reaction components is soluble in water, and especially when the source of oxygen is sodium hypochlorite.

Suitable two phase systems are those used conventionally in the art taking into account the nature of the particular reactants, an example is methylene chloride and water.

The salen catalyst such as a compound of formula (I), (IA), (II) or (III), the prochiral olefin and the source of the electron donating ligand in an inert, water immiscible solvent such as dichloromethane may be reacted with the source of oxygen in water.

Generally the reaction takes place at a pH in the range of between 10 and 13, preferably between 10.5 and 12, most preferably between 11 and 11.5, conveniently the pH is controlled by the presence of a buffer such as sodium dihydrogen phosphate.

The reaction may be carried out at any suitable temperature providing a convenient rate of formation of the required product. Because of the increase in rate of the reaction caused by the presence of the source of the electron donating ligand the reaction may be carried out at a lower temperature than without the said ligand, such as in the range of between 0° C. and 40° C.

Generally it is carried out at ambient or at a slightly elevated temperature but preferably at ambient temperature.

Suitably the mole percentage ratio of the compound of formula (I) to the prochiral olefin is in the range of 0.01 to 10, preferably in the range of 0.1 to 0.5, 0.5 to 5, 1 to 5, 1 to 3, 0.5 to 2 most preferably in the range of 0.2 to 2.

Suitably the mole ratio of the source of the electron donating ligand to prochiral olefin is in the range of 0.05 to 3, such as 0.1 to 2.0 or 1 to 2, preferably in the range of 0.1 to 2. For example a suitable more range for N-pyridine oxide is 0.5 to 2. An example of a suitable mole ratio range for isoquinoline N-oxide is 0.1 to 0.5.

The present invention also extends to the preparation of all epoxides which are precursors to those compounds of formula (I) in WO 92/22293, especially the specific examples thereof.

The present invention also extends to the preparation of all epoxides which are precursors to those compound of formula (I) in EP-A- 0376524, especially the specific examples thereof.

The present invention also extends to the subsequent conversion of each of the said epoxides into the respective compounds of formula (I) of EP-A-0 376 524, in particular to the conversion of the relevant precursor epoxide into the respectively specific example of EP-A-0 376 524, and especially to the conversation of 2,2-dimethyl-6-pentafluoroethyl-3,4-epoxy-2H-1-benzopyran into (–) trans-3,4-dihydro-2,2-dimethyl-4-(2-oxopiperidin-1-yl)-6-pentafluoroethyl-2H-1-benzopyran-3-ol or the (+) trans isomer thereof.

The present invention also extends to the subsequent conversion of each of the said epoxides into the respective compounds of formula (I) of WO 92.22293, in particular to the conversion of the relevant precursor epoxide into the respective specific example of WO 92/22293 and in particular to the conversion of (3R, 4R) 6-acetyl-2,2dimethyl-3,4-epoxy-2H-1-benzopyran into trans-6-acetyl-4S-(4-fluorobenzoylamino)-3,4-dihydro-2,2-dimethy-2H-1-benzopyran-3R-ol or the 3S, 4R isomer thereof.

The present invention also extends to the product formed between the salen catalyst, such as the compound of formula (I), (IA), (IB), (II) or (III) and the electron donating ligand.

When used herein the term 'chiral salen catalyst' refers to salen catalysts which have a predominance of one particular enantiomer and which in use provide a predominance of one particular enantiomer of the product epoxide from the prochiral olefin substrate.

The term 'alkyl' when used alone or when forming part of other groups (for example alkoxy groups or alkycarbonyl groups) includes straight- or branched-chain alkyl groups containing 1 to 12 carbon atoms, suitably 1 to 6 carbon atoms, examples include methyl, ethyl, n-propyl, isopropyl, n-butyl, isobutyl or tert-butyl group.

When used herein the term 'aryl' includes phenyl and naphthyl optionally substituted with up to five, preferably up to three, groups selected from halogen, alkyl, phenyl, alkoxy, haloalkyl, alkylcarbonyl and phenylcarbonyl.

A preferred aryl group is a substituted or unsubstituted phenyl group.

Transition metals M include those having oxidation states of (II) or more.

Suitable substituents for aryl include alkyl, halogen and alkoxy.

Optional substituents for alkyl groups include those mentioned herein for aryl groups, phenyl is a particular example.

It should be appreciated that the carbon atoms marked with an asterisk are chiral centres and the present invention extends to each individual enantiomer and any mixtures thereof.

The compounds of formula (I), (IA) and (IB) may be prepared according to the procedures in described in WO 91/14694 or by procedures analogous to them.

The compounds of formula (II) may be prepared according to the procedures disclosed in International Application, Publication Number WO 91/14694 or procedures analogous the them.

The contents of WO 91/14694 and WO 94/03271, including the specific descriptions and examples therein, are incorporated herein by reference.

For the compounds of formula (III), the present invention also provides a process for the preparation of compounds of formula (III) which comprises forming a transition metal complex of the following compound of formula (IV):

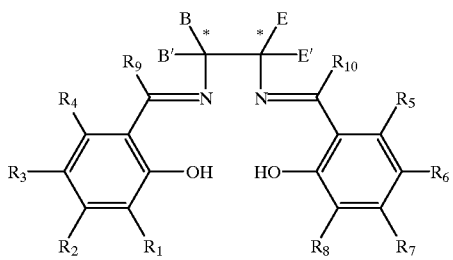

where variables $R_1$, $R_2$, $R_3$, $R_4$, $R_5$, $R_6$, $R_7$, $R_8$, $R_9$ and $R_{10}$, B, B', E and E' are as defined in relation to formula (III), wherein only one of the carbons marked with an asterisk is a chiral centre, and thereafter if necessary separating any enantiomers.

Suitably the transition metal ion complex may be formed by the addition of a suitable transition metal salt, such as manganese (II) or (III) acetate, preferably manganese (III) acetate, to a compound of formula (IV) in a suitable solvent such as ethanol or methylene dichloride, at elevated temperature. The optional replacement or interconversion of the counter ion may be effected by the addition of a suitable source of the desired counter-ion such as an alkali metal salt, for example LiCl.

The separation of any enantiomers may be carried out by conventional techniques, such as crystallisation of derivatives or chromatography. However, it should be appreciated that it is preferred that separation of enantiomers is carried out before forming a transition metal complex.

The invention further provides a process for the preparation of compounds of formula (IV) which comprises condensing sequentially, in any order, a compound of formula (V):

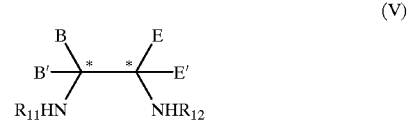

where B, B', E and E' are as defined in formula (III) and $R_{11}$ and $R_{12}$ independently represent hydrogen or an amine protecting group, providing at least one of $R_{11}$ and $R_{12}$ is hydrogen, with:

(i) a compound of formula (VI);

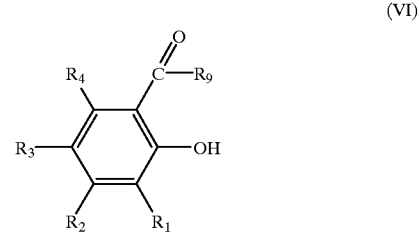

wherein $R_1$, $R_2$, $R_3$, $R_4$ and $R_9$ are as defined in relation to formula (III); and (ii) a compound of formula (VII),

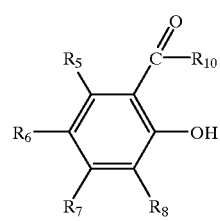

wherein $R_5$, $R_6$, $R_7$, $R_8$ and $R_{10}$ are as defined in relation to formula (III); and thereafter as required removing any protecting group $R_{11}$ or $R_{12}$ isolating the required compound including if necessary separating any enantiomers.

It is preferred that the compound of formula (IV) is prepared from optically pure compounds of formula (V) which are preferably prepared themselves from optically pure starting materials. Alternatively, racemates or mixtures of enantiomers of formula (VI) or (VII) may themselves be resolved using conventional techniques in the art such as crystallisation of derivatives, or chromatography.

When compounds of formula (IV) are required in which one or more of $R_1$, $R_2$, $R_3$, $R_4$ and $R_9$ are not the same as one or more of $R_8$, $R_7$, $R_6$, $R_5$ and $R_{10}$ respectively, then compounds of formula (V) may be sequentially condense with compounds of formula (VI) and formula (VII), in any order, by heating a suitably protected compound of formula (V) with a compound of formula (VI) or (VIII) (in a 1:1 mole ratio) in an inert solvent such as ethanol, if necessary, purifying the resulting intermediate compound of formula (VIII) or (IX);

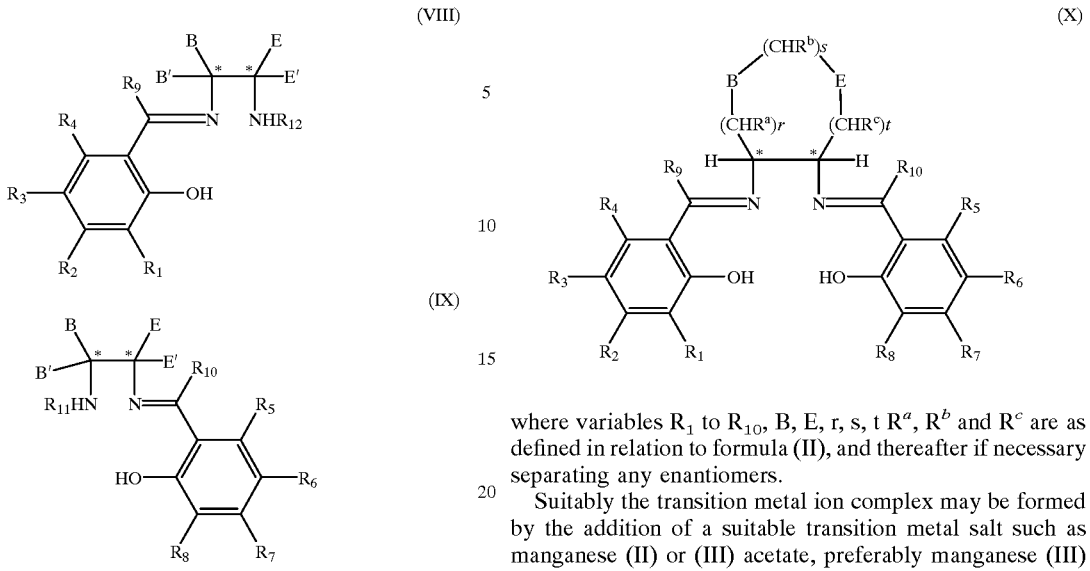

(VIII)

(IX)

wherein variables $R_1$ to $R_{12}$, E, E', B and B' are as defined in relation to formula (V), (VI) or (VII) using conventional separation techniques, such as chromatography; removing any protecting group $R_{11}$ or $R_{12}$ and then as required repeating the reaction using a compound of formula (VI) or (VII).

Suitable protecting groups $R_{11}$ or $R_{12}$ include conventional amine protecting groups the insertion and removal of which are compatible with the nature of the molecules being protected, such as benzyl groups, silyl groups or acyl groups such as benzoyl groups, preferably silyl groups.

The removal of $R_{11}$ or $R_{12}$ when representing protecting groups may be carried out using conventional techniques in the art depending upon the nature of the protecting group.

It should be appreciated that when each of $R_1$, $R_2$, $R_3$, $R_4$ and $R_9$ is the same as each of $R_8$, $R_7$, $R^6$, $R^5$ and $R_{10}$ respectively the compounds of formula (VI) and (VII) are the same, therefore, compounds of formula (V) in which $R_{11}$ and $R_{12}$ is hydrogen are preferably used and two moles of a compound of formula (VI) or (VII) are utilised.

Suitably, the reaction is carried out in an inert solvent, such as ethanol, at elevated temperature, for example at reflux temperature of the chosen solvent.

Compounds of formula (V) are either known compounds or may be prepared according to known methods of analogously to known methods or analogously to the methods described herein.

Compounds of formula (VI) and (VII) are either commercially available, are known compounds or may be prepared according to known methods or analogously to known methods for examples such as these described by G. Casiraghi et al J. Chem Soc. Perkin Transactions I. 1980 p1862–1865.

Novel compounds of formula (IV), (VI), (VII), (VIII) and (IX) form an aspect of the present invention.

As stated above the compounds of formula (II) herein may be prepared using the methods disclosed in co-pending International Patent Application Number PCT/GB93/01666 (now International Patent Application, Publication Number WO 94/03271). For the avoidance of doubt these methods involve the following:

The compounds of formula (II) may be prepared by forming a transition metal complex of the following compound of formula (X):

(X)

where variables $R_1$ to $R_{10}$, B, E, r, s, t $R^a$, $R^b$ and $R^c$ are as defined in relation to formula (II), and thereafter if necessary separating any enantiomers.

Suitably the transition metal ion complex may be formed by the addition of a suitable transition metal salt such as manganese (II) or (III) acetate, preferably manganese (III) acetate, to a compound of formula (II) in a suitable solvent such as ethanol or methylene dichloride, at elevated temperature. The optional replacement or interconversion of the counter ion may be effected by the addition of a suitable source of the desired counter-ion such as an alkali metal salt, for example LiCl.

The separation of any enantiomers may be carried out by conventional techniques, such as crystallisation of derivatives or chromatography. However, it should be appreciated that is is preferred that separation of enantiomers is carried out before forming a transition metal complex.

The compounds of formula (X) may also be prepared by condensing sequentially, in any order, a compound of formula (XI):

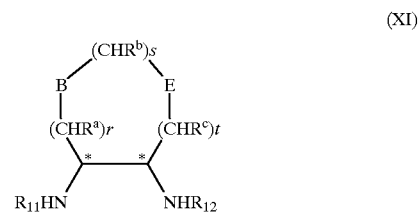

(XI)

where r, s, t, $R^a$, $R^b$ and $R^c$ E, B are as defined in formula (II) and $R_{11}$ and $R_{12}$ independently represent hydrogen or an amine protecting group, providing at least one of $R_{11}$ and $R_{12}$ is hydrogen, with a compound of the above defined formulae (VI) and (VII). The reaction conditions are analogous to those mentioned above in relation to the reaction between the compound of formula (V) and the compounds of formulae (VI) and (VII).

It is preferred that the compound of formula (X) is prepared from optically pure compounds of formula (XI) which are preferably prepared themselves from optically pure starting materials. Alternatively, racemates or mixtures of enantiomers of formula (X) or (XI) may themselves be resolved using conventional techniques in the art such as crystallisation of derivatives, or chromatography.

When compounds of formula (X) are required in which one or more of $R_1$, $R_2$, $R_3$, $R_4$ and $R_9$ are not the same as one or more of $R_8$, $R_7$, $R_6$, $R_5$ and $R_{10}$ respectively, then compounds of formula (XI) may be sequentially condensed with compounds of formula (VI) and formula (VII), in any order, by heating a suitably protected compound of formula (XI) with a compound of formula (VI) or (VII) (in a 1:1 mole ratio) in an inert solvent such as ethanol, if necessary, purifying the resulting intermediate compound of formula (XII) or (XIII):

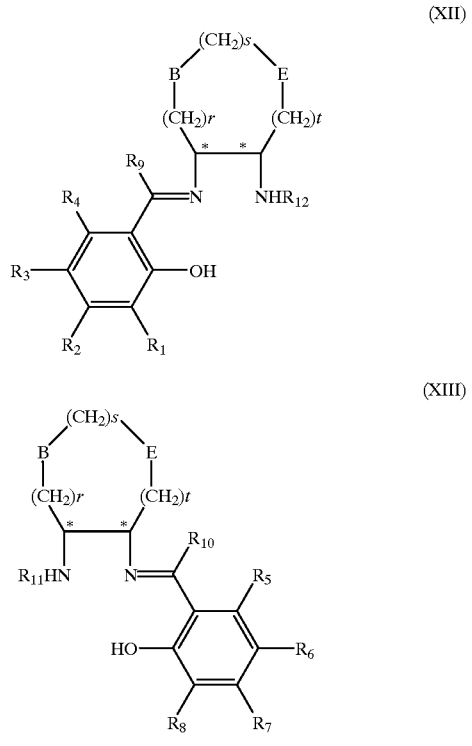

wherein variables $R_1$ to $R_{12}$, r, s, t, $R^a$, $R^b$, $R^c$, E and B are as defined in to formula (XI), (VI) and (VII) using conventional techniques such as chromatography removing and $R_{11}$ or $R_{12}$ protecting groups and then repeating the reaction using a compound of formula (VI) or (VII) as required.

Suitable protecting groups $R_{11}$ and $R_{12}$ and the methods for the removal of such groups are as described above.

It should be appreciated that when each of $R_1$, $R_2$, $R_3$, $R_4$ and $R_9$ is the same as each of $R_8$, $R_7$, $R_6$, $R_5$ and $R_{10}$ respectively the compounds of formula (VI) and (VII) are the same, therefore, compounds of formula (XI) in which $R_{11}$ and $R_{12}$ is hydrogen are preferably used and two moles of a compound of formula (VI) or (VII) are utilised, in an inert solvent, such as ethanol, at elevated temperature, for example at reflux.

Compounds of formula (XI) are either known compounds or may be prepared according to known methods or analogously to known methods or analogously to the methods described herein, for example when a compound of formula (XI) is 3,4-diaminotetrahydrofuran, such a compound may be prepared according to the following scheme, for example, as described in descriptions 1 and 2.

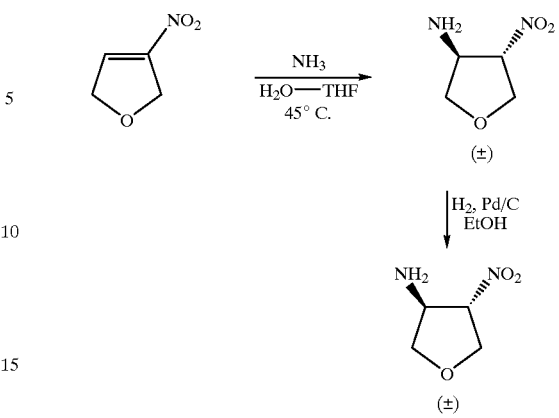

Alternatively, (S,S)trans 3,4-diaminotetrahydrofuran may be prepared according to the following scheme, for example, as described in descriptions 4 to 6.

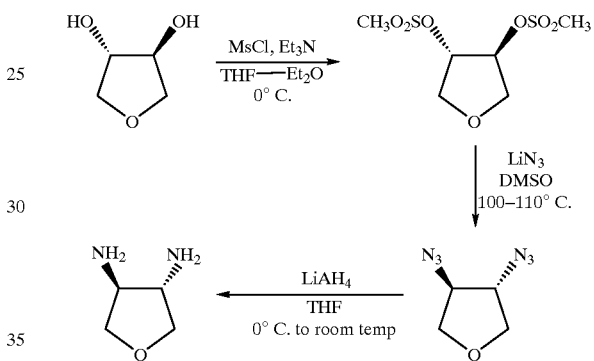

The 5R, 6R-diamino-1,3-dioxepane may be prepared according to the procedures, as described in descriptions 8 to 13.

The 3R, 4S-diamino tetrahydropyran may be prepared according to the procedures as described in descriptions 15 to 17.

The 3R,4S-diamino-(2S)(triphenylmethoxymethyl) tetrahydropyran may be prepared according to the procedures as described in descriptions 21 to 24.

The (±) trans-I-benzoyl-3,4-diaminopiperidine may be prepared according to the procedures as described in descriptions 25 to 27.

The catalysts, of formula (III) are preferably prepared in a chiral form by using a resolved compound of formula (XI) which may be resolved using conventional techniques. The compound of formula (XI) may itself be prepared from suitable precursor compounds such as these outlined in hereinbefore which may be resolved using conventional techniques or may be purchased in a resolved form. Alternatively, the coupled compound of formula (X) may be resolved using conventional techniques.

The present invention also provides a process for preparing compounds of formula (A) (as defined in WO 93 17026) or, where appropriate, a pharmaceutically acceptable salt thereof, or a pharmaceutically acceptable solvate thereof which comprises reacting a compound of formula (I), a source of oxygen, a compound of formula (C) and a source of the electron donating ligand, thereafter converting the resulting compound of formula (B) into a compound of formula (A) or, where appropriate, a pharmaceutically acceptable salt thereof, or a pharmaceutically acceptable solvate thereof.

The present invention also extends to the product formed between the compound of formula (I) and the electron donating ligand provided by the above mentioned source.

Compounds of formula (C) are commercially available or may be prepared according to the procedures referred to or outlined in EP-A-0 376 524.

The following descriptions and examples illustrate the present invention.

(A) Examples Using the Catalysts of WO 91/14694

Example 1

The Preparation of (3R,4R)-6-Acetyl-2,2-Dimethyl-3,4-Epoxy-2H-1-Benzopyran, Using Pyridine N-Oxide as Electron Donating Ligand A solution of sodium hypochlorite (54 ml, 13.7% w/v), 0.05M NaHPO$_4$ (50 ml) and water (70 ml) were adjusted to pH 11.3 with 8N NaOH. 6-Acetyl-2,2-dimethyl chromene (10 g 0.049 mol) and R,R-[1,2-bis(3,5-di-tert-butylsalicylideamino)cyclo-hexane]manganese (III) chloride catalyst (320 mg 1 mol %), pyridine N-oxide (9.5 g, 2 eq) and dichloromethane (50 ml) were mixed together and the mixture was stirred for 1 hour.

The solution was diluted with DCM (200 ml) and filtered through celite and the layers separated. The aqueous layer was re-extracted with DCM (200 ml) then the organic layers combined. The organic phase was washed with water (2×400 ml) and evaporated to dryness to give a brown oil 12 g, ee 95% (chiral hplc). The oil was crystallised from IPE (2½ volumes) seeded with epoxide to give the title compound as an off-white/brown solid (6.45 g, 60%) ee>99%.

The same reaction without an electron donating ligand added, such as pyridine N-oxide, typically requires 1 mole % of catalyst to achieve complete conversion at room temperature in about 4 hrs (crude epoxide e.e. 92%).

Example 2

The Preparation of (3R,4R)-2,2-Dimethyl-3,4-Epoxy-6-Pentafluoroethyl-2H-1-Benzopyran, Using Isoquinoline N-Oxide as Electron Donating Ligand A solution of sodium hypochlorite (44 ml, 17% w/v), water (70 ml) and 0.05M NaH$_2$PO$_4$ (50 ml) was adjusted to pH 11.3 with dilute orthophosphoric acid. 2,2-Dimethyl-6-pentafluoroethyl-2H-1-benzopyran (13.6 g, 50 mmol), dichloromethane (100 ml), isoquinoline N-oxide (0.725 g, 10 mole %) and R,R-[1,2-bis(3,5-di-tert-butylsalicylideamino)cyclohexane]manganese (III) chloride (64 mg, 0.2 mole %) were added and the mixture stirred rapidly at room temperature. After 2 hrs HPLC analysis indicated 95% conversion of chromene to epoxide. The reaction mixture was allowed to stir at room temperature for another 3 hrs but no further conversion of chromene to epoxide occurred. The e.e. of the crude (3R,4R)-epoxide was measured as 92.5% according to chiral HPLC. The mixture was diluted with dichloromethane (200 ml) and filtered through celite, and the layers separated. The organic phase was washed with water (3×100 ml) then evaporated to dryness to give the crude title compound (15.0 g), as a yellow solid. The crude product was recrystallised from hexane (3 volumes) to give the pure title compound (8.0 g, 54%) as colourless needles (e.e.>99%).

The same reaction without an electron donating ligand, such as isoquinoline N-oxide, typically requires 2 mole % of catalyst to give complete conversion.

Example 3

The Preparation of (3R,4R)-6-Acetyl-2,2-Dimethyl-3,4-Epoxy-2H-1-Benzopyran, Using Isoquinoline N-Oxide as Electron Donating Ligand The procedure of Example 1 was repeated using 10 mole % of isoquinoline N-oxide instead of pyridine N-oxide. The amount of catalyst was also reduced to 0.1 mole %. Complete conversion to the required epoxide (e.e. 96%) was achieved in less than 15 mins.

Example 4

The Preparation of (3R,4R)-6-Acetyl-2,2-Dimethyl-3,4-Epoxy-8-iodo-2H-1-Benzopyran, Using Isoquinoline N-Oxide as Electron Donating Ligand The procedure of Example 1 was repeated using 0.2 equiv of isoquinoline N-oxide instead of pyridine N-oxide. The amount of catalyst was reduced to 0.2 mole %. Complete conversion to the epoxide (e.e. 98%) was observed after 2 hrs. The crude product was recrystallised from IPE (3 volumes) to give the enantiomerically pure title compound, m.p. 123.6–125.4 deg. C., in a yield of 72%.

(B) Examples Using the Catalysts of WO 94/03271

Example 5

Preparation of (3R,4R)-6-Acetyl-2,2-Dimethyl-3,4-Epoxy-2H-1-Benzopyran, Using Pyridine N-Oxide as Electron Donating Ligand Sodium hypochlorite (21.5 ml, 17.3% w/v), water (34 ml) and 0.05M Na$_2$HPO$_4$ (25 ml) were adjusted to pH 13 with 8N NaOH. 6-Acetyl-2,2-dimethyl-2H-1-benzopyran (5.0 g, 25 mmoles), pyridine N-oxide (5.0 g, 52 mmoles) and the S,S-Mn Salen catalyst (3S,4S)-bis-(3,5-di-tert-butylsalicylideamino)tetrahydrofuran-manganese (III) chloride (D34, 152 mg, 1 mole %) were added with dichloromethane (50 ml) and the mixture stirred at room temperature. After 2 hrs the reaction was complete according to HPLC analysis. The mixture was diluted with dichloromethane and filtered through celite. The two phases were separated and the organic phase washed with water (200 ml), then evaporated to dryness under reduced pressure to give the crude title compound as a brown oil (5.0 g). This was shown by chiral HPLC to have an e.e. of 94%.

The title compound was obtained enantiomercially pure (e.e.>99.8%) by recrystallization of the crude product from diisopropyl ether in a recovery of 44%.

Example 6

Preparation of (3S,4S)-6-Acetyl-2,2-Dimethyl-3,4-Epoxy-2H-1-Benzopyran Without Use of an Electron Donating Ligand Sodium hypochloride solution (8.0 ml, 17.3% w/v), water (14 ml) and 0.05M Na$_2$HPO$_4$ (10 ml) was adjusted to pH 13 with 8N NaOH. 6-Acetyl-2,2-dimethyl-2H-1-benzopyran (2.0 g, 10 mmoles) and R,R-Mn Salen catalyst (R,R)-5,6-bis-(3,5-di-tert-butylsalicylideamino)-1,3-dioxepane]-manganese (III) chloride (D31, 63 mg, 1 mol %) were added with dichloromethane (20 ml) and the mixture stirred at room temperature overnight. HPLC analysis indicated that about 13% of the chromene still remained.

The mixture was diluted with dichloromethane (50 ml) and filtered through celite. The organic phase was separated then washed with water (100 ml) and evaporated to dryness to give the crude title compound as an oil (2.1 g, 96% wt. yield). Analysis of this sample by chiral HPLC indicated an e.e. of 86%.

Example 7

Preparation of (3S,4S)-6-Acetyl-2,2-Dimethyl-3,4-Epoxy-2H-1-Benzopyran, Using Pyridine-N-Oxide as Electron Donating Ligand The procedure of Example 6 was repeated but with the addition of pyridine N-oxide (1.9 g, 20 mmoles). HPLC analysis indicated complete reaction after stirring overnight at room temperature. The crude product was isolated in the same way to give 2.3 g of the title compound with an e.e. of 95%. The title compound was obtained enantiomerically pure (e.e.>99.8%) by recrystallization of the crude product from diisopropyl ether in a recovery of 50%.

Example 8

Preparation of (3R,4R)-6-Acetyl-2,2-Dimethyl-3,4-Epoxy-2H-1-Benzopyran, Using Isoquinoline-N-Oxide as Electron Donating Ligand The procedure of Example 5 was repeated but with the addition of isoquinoline-N-oxide (1.74 g, 12 mmoles) instead of pyridine N-oxide. HPLC analysis indicated complete reaction within 30 mins., after stirring at room temperature. The crude product was isolated in the same way to give the crude title compound as a brown oil (5.1 g). This was shown by chiral HPLC to have an e.e. of 94%. The title compound was obtained enantiomerically pure (e.e.>99.8%) by recrystallization from diisopropyl ether in a recovery of 48%.

Example 9

Preparation of (3S,4S)-6-Acetyl-2,2-Dimethyl-3,4-Epoxy-2H-1-Benzopyran

Sodium hypochloride (31 ml, 12.1% w/v, 50 mmoles), water (34 ml) and 0.05M $Na_2HPO_4$ (25 ml) were adjusted to pH 13 with 8N NaOH. 6-Acetyl-2,2-dimethyl-2H-1-benzopyran (5.0 g, 25 mmoles), isoquinoline N-oxide (0.362 g, 5 mmoles, 0.2 equiv) and (3R,4S)-bis-(3,5-di-tert-butylsalicylideamino)tetrahydropyran manganese (III) chloride (0.032 g, 0.05 mmole, 0.2 moles %) were added with dichloromethane (50 ml) and the mixture stirred at 15–20 deg. C. After 4 hrs the reaction was complete according to HPLC analysis. The mixture was diluted with dichloromethane and filtered through celite. The two phases were separated and the organic phase washed with water (2×200 ml), then evaporated to dryness under reduced pressure to give the crude title compound as a pale brown oil (5.3 g). This was shown by chiral HPLC to have an e.e. of 92%.

The title compound was obtained enantiomercially pure (e.e.>99.8%), m.p. 51° C., by recrystallization of the crude product from diisopropyl ether in a recovery of 41%.

Example 10

Preparation of (3S,4S)-6-Cyano-2,2-Dimethyl-3,4-Epoxy-2H-1-Benzopyran

The procedure described in Example 9 was repeated using 6-cyano-2,2-dimethyl-2H-1-benzopyran (4.63 g, 25-mmoles) as the chromene substrate. The crude (3S,4S) epoxide formed was shown to have an e.e. of 95%. This was recrystallised from 2-propanol to give the title compound (e.e.>99%), m.p. 144–145 deg. C., in a recovery of 75%.

Example 11

Preparation of (3S,4S)-6-Bromo-2,2-Dimethyl-3,4-Epoxy-2H-1-Benzopyran

The procedure described in Example 9 was repeated using 6-bromo-2,2-dimethyl-2H-1-benzopyran (5.98 g, 25 mmoles) as the chromene substrate. The crude (3S,4S) epoxide formed was shown to have an e.e. of 95%. This was recrystallised from hexane/ethyl acetate to give the title compound (e.e.>99%), m.p. 101–102 deg. C., in a recovery of 65%.

(C) Examples Using The Compound of Formula (III) as Catalyst

Example 12

(R)-1-Phenyl-1,2-Bis(3-Tert-Butyl-5-Methylsalicylideamino)Ethane-Manganese (III) Chloride (E12)

(R)-1-Phenyl-1,2-bis(3-tert-butyl-5-methylsalicylideamino)ethane (D37, 2.42 g, 5.0 mmol) was dissolved in ethanol (50 ml) and solid manganese (II) acetate tetrahydrate (2.45 g, 10.0 mmol) was added. The solution was refluxed for 2 hours then lithium chloride (anhydrous) 0.64 g, 15.0 mmol) was added and the solution was refluxed for a further 30 min. After cooling water (1 ml) was added to the stirring solution. The precipitate was removed by filtration, washed with 90% aqueous ethanol (10 ml) then dried in vacuo over $P_2O_5$ to afford the title compound as a brown solid, 2.73 g, 95% yield.

Example 13

The Chiral Epoxidation of 2,2-Dimethyl-6-Pentafluorethylchromene Using E12 to Give 2,2-Dimethyl-6-Pentafluoroethyl-1H-Benzopyran-(3R, 4R)-Epoxide Aqueous sodium hypochlorite solution (8.5% w/v, 17.5 ml, 20.0 mmol) was diluted to 25 ml with water followed by the addition of 0.05M $NaH_2PO_4$ (aq) (10 ml). The pH was adjusted to 11.3 and the solution cooled to 0° C., then added to a solution of 2,2-dimethyl-6-pentafluoroethyl chromene (2.78 g, 10.0 mmol) and (E12) (0.115 g, 0.20 mmol) in methylene chloride (10 ml) at 0° C. The reaction was stirred for 1 hour at 0° C. then at room temperature overnight.

Hexane (100 ml) and water (50 ml) were added and the organic layer partitioned off. The aqueous layer was extracted with a further portion of hexane (100 ml) and the combined organic layer was dried over $MgSO_4$ and the solvent removed in vacuo to give the title compound as a brown oil, 2.7 g (94% yield).

The oil was purified by flash chromatography (silica gel 60, MERCK 9385, 230–400 mesh) (30 g) eluting with 0–5% diethylether in hexane to give the title compound as a pale yellow, partially crystalline solid, 2.11 g, 72% yield, identical ($^1$H NMR, TLC, HPLC) with an authentic sample, e.e.=63% by chiral HPLC.

Example 14

(R)-1-Phenyl-1,2-Bis(3,5-Di-Tert-Butylsalicylideamino)Ethane-Manganese (III) Chloride (E14)

(R)-1-Phenyl-1,2-bis(3,5-di-tert-butylsalicylideamino) ethane (D38, 1.70 g, 3.0 mmol) was dissolved in ethanol (30 ml) and manganese (II) acetate tetrahydrate (1.47 g, 6.0 mmol) was added. The solution was refluxed for 16 hours then lithium chloride (0.38 g, 9.0 mmol) was added, the reaction refluxed for a further 30 min then allowed to cool to room temperature. Water (1 ml) was added to the stirring solution and the resulting precipitate was removed by filtration to give the product as a brown solid which was dried in vacuo over $P_2O_5$ to afford 2.56 g of the title compound, 78% yield.

Example 15

The Chiral Epoxidation of 2,2-Dimethyl-6-Pentafluorethylchromene Using E14 to Give 2,2-Dimethyl-6-Pentafluoroethyl-1H-Benzopyran-(3R, 4R)-Epoxide Aqueous sodium hypochlorite solution (8.5% w/v, 17.5 ml, 20.0 mmol) was diluted to 25 ml with water followed by the addition of 0.05M $NaH_2PO_4$ (aq) (10 ml). The pH was adjusted to 11.3 and the solution cooled to 0° C., then added to a solution of 2,2-dimethyl-6-pentafluoroethyl chromene (2.78 g, 10.0 mmol) and (R)-1-phenyl-1,2-bis(3,5-di-tert-butyl-salicylideamino)ethane-manganese (III) chloride (E14) (0.131 g, 0.20 mmol) in methylene chloride (10 ml) at 0° C. The reaction was stirred for 2 hours at 0° C. then at room temperature overnight.

Hexane (100 ml) and water (50 ml) were added and the organic layer partitioned off. The aqueous layer was extracted with a further portion of hexane (100 ml), and the combined organic layers was dried over $MgSO_4$ and the solvent removed in vacuo to give the title compound as a yellow oil, 2.91 g (99% yield).

The oil was purified by flash chromatography (silica gel 60, MERCK, 230–400 mesh) (40 g) eluting with 0–5% diethyl ether in hexane to give the title compound as a pale yellow crystalline solid, 1.81 g, 62% yield, identical ($^1$H NMR, TLC, HPLC) with an authentic sample, ee=68% by chiral HPLC.

Example 16

(S)-1-Methyl-1,2-Bis(3-Tert-Butyl-5-Methylsalicylideamino) Ethane-Manganese (III) Chloride (E16)

(S)-1-Methyl-1,2-bis(3-tert-butyl-5-methylsalicylideamino)ethane (D39) (338 mg, 0.8 mmol) was dissolved in EtOH (8 ml) and manganese (II) acetate tetrahydrate (392 mg, 1.6 mmol) was added. The mixture was refluxed for 2 h then lithium chloride (102 mg, 2.4 mmol) was added and, after a further 1 h at reflux, the mixture was cooled to ambient. A few drops of water were added and the resulting precipitate filtered and dried in vacuo over $P_2O_5$ to afford the title compound as a brown powder, 270 mg (66% yield).

Example 17

The Chiral Epoxidation of 2,2-Dimethyl-6-Pentafluorethyl Chromene Using E16 to Give 2,2-Dimethyl-6-Pentafluoroethylchromene-(3S,4S)-Epoxide Aqueous sodium hypochlorite solution (16.75% w/v, 8.9 ml, 20 mmol) was diluted to 25 ml with water followed by the addition of 0.05m $NaH_2PO_4$ (aq) (10 ml). The pH was adjusted to 11.3 and the solution cooled to 0° C., then added to a solution of 2,2-dimethyl-6-pentafluorethyl chromene (2.78 g, 10 mmol) and (S)-1-methyl-1,2-bis(3-tert-butyl-5-methylsalicylideamino)ethane-manganese (III) chloride (E16, 102 mg, 0.20 mmol) in methylene chloride (10 ml) at 0° C. The reaction was stirred at 0° C. for 1 h then at room temperature overnight.

Hexane (100 ml) and water (50 ml) were added and the organic layer partitioned off. The aqueous layer was extracted with a further portion of hexane (100 ml) and the combined organic layers were dried over $MgSO_4$ and the solvent removed in vacuo to give the crude title compound as a brown oil, 2.78 g (95% yield). Quantitative analysis (HPLC) showed this to contain 2.27 g (77% yield) of the title compound, identical (TLC, HPLC) with an authentic sample, ee=32% by chiral HPLC.

Example 18

(S)-1-Isopropyl-1, 2-bis (3-tert-butyl-5-methylsalicyclideamino) ethane-manganese (III) chloride (E18)

(S)-1-isoPropyl-1, 2-bis (3-tert-butyl-5-methylsalicylideamino) ethane (D40, 240 mg, 0.53 mmol) was dissolved in ethanol (10 ml) and manganese (III) acetate dihydrate (0.14 g), 0.53 mmol) was added. The mixture was refluxed for 2 h then lithium chloride (34 mg, 0.8 mmol) was added. After a further 1 h at reflux the solution was cooled, solvent was removed in vacuo and the residue chromatographed on silica (Merck 9385, 20 g, eluting with 0–6% methanol in chloroform) to afford the title compound as a brown powder, 60 mg (21% yield).

Example 19

The chiral epoxidation of 2, 2-dimethyl-6-pentafluorethyl chromene using E18 to give 2, 2-dimethyl-6-pentafluoroethylchromene-(3S, 4S)-epoxide Aqueous sodium hypochlorite solution (15.24% w/v, 2 ml, 4 mmol) was made up to 5 ml with water. 0.05 M $NaH_2PO_4$(aq) (2 ml) was added and the pH adjusted to 11.3. The solution was cooled to 0° C. then added to a solution of (0.56 g, 2 mmol) and the catalyst (S)-1-isopropyl-1, 2-bis (3-tert-butyl-5-methylsalicyclideamino) ethane-manganese (III) chloride. (E18, 21.5 mg, 0.04 mmol) in methylene chloride (6 ml). The mixture was stirred at 0° C. for 1 then at room temperature overnight.

Hexane (20 ml) and water (10 ml) were added and the organic layer separated. The aqueous phase was extracted with further hexane (20 ml) and the combined organic phase was dried ($MgSO_4$) and the solvent removed in vacuo to afford the title compound as a yellow oil (0.51 g). Quantitative analysis (HPLC) showed this to contain 0.42 g (71% yield) of the title compound, identical (TLC, HPLC) with an authentic sample, ee=23% by chiral HPLC.

Example 20

The chiral epoxidation of 6-acetyl-2, 2-dimethyl chromene using E14 to give 6-acetyl-2, 2-dimethyl chromene-(3R, 4R) epoxide A solution of sodium hypochlorite (8.6 ml, 17.3% w/v), water (14 ml) and $Na_2HPO_4$ (0.05M, 10 ml) was adjusted to pH 11.3 with 8N NaOH. 6-Acetyl-2,2-dimethyl chromene (2 g) and E14 (65.6 mg 1 mol %) and dichloromethane (20 ml) was added and the mixture stirred rapidly at room temperature overnight.

The mixture was diluted with dichloromethane (50 ml) and filtered through celite. The two layers were separated and the organic phase washed with water (100 ml) the evaporated to dryness to give the title compound (2.0 g 92%), ee=67% by chiral HPLC.

Example 21

The chiral epoxidation of 6-acetyl-2, 2-dimethyl chromene using E14 ti give 6-acetyl-2, 2-dimethyl chromene-(3R, 4R) epoxide, using pyridine-N-oxide as electron donating catalyst The reaction of Example 20 was repeated with the addition of pyridine N-oxide (1.9 g, 2 eq). The ee of the title product was found to be 79% using chiral HPLC.

Descriptions of Intermediates for the Preparation of Compounds of Formula (II) (as described in WO 94/03271)

Description 1

(±) 2,5-Dihydro-3-nitrofuran (D1)

A mixture of (±) trans 3-chloromercurio-4-nitro-2,5-dihydrofuran[1] (38.54 g, (109.6 mmol) and $Et_3N$ (11.07 g, 109.6 mmol) in $CH_2Cl_2$ (2.2 L) at 25° C. was stirred for 1.25 h. 5% aqueous citric acid (1.1 L) was added and stirring was continued for 5 min. The mixture was filtered through celite, separated and the organic phase washed with 5% aqueous citric acid (220 ml), dried over $Na_2SO_4$ and concentrated in vacuo. Chromatography of the residue on silica (Merck 9385, 300 g) eluting with $CHCl_3$-Hexane (1:1–>1:0) afforded (D1) as a pale yellow oil which crystallized in the freezer, 5.45 g (43.2%).

δ ($CDCl_3$) 4.95 (4H,S) and 7.10 (1H,S)

1. P Bitha and Y—I. Lin, *J. Heterocyclic Chem.*, 1988, 25, 1035–1036.

Description 2

(±) 3,4-Diaminotetrahydrofuran (D2)

A solution of (±) 4-amino-3-nitrotetrahydrofuran, prepared from (D1) via the method of Bitha and Lin[1], (4.66 g, 35.3 mmol) in EtOH (100 ml) containing 10% palladium on carbon (2.5 g) was hydrogenated on a Parr shaker apparatus at 35 psi for 65 h at 20° C. The suspension was filtered, the solids washed with EtOH (100 ml) and the combined filtrate evaporated in vacuo to afford (±) (D2) as a colourless oil, 3.26 g (81.5%).

δ ($CDCl_3$) 1.40 (4H,bs), 3.20 (2H,m), 3.50 (2H,dd) and 4.08 (2H,dd).

Description 3

(±) 3,4-bis (3-tert-Butyl-5-methylsalicylideamino) tetrahydrofuran (D3)

A solution of the racemic diamine (D2) (855 mg, 8.38 mmol) and 3-tert-butyl-5-methylsalicaldehyde (3.22 g), 16.76 mmol) in EtOH (50 ml) was heated at reflux for 1.5 h. The solvent was removed in vacuo and the residue chromatographed on silica (Merck 9385, 300 g) using $CHCl_3$ as eluent to afford (±) (D3) as pale yellow needles, 1.35 g, (35.8%).

δ ($CDCl_3$) 1.42 (18H,s), 2.25 (6H,s), 3.95–4.10 (2H, m), 4.43 (2H, q), 6.90 (2H,d), 7.15 (2H,d), 8.30 (2H,s) and 13.10 (2H,bs).

Description 4

(S,S) trans 3,4-bis(methanesulphonyloxy) tetrahydrofuran (D4)

A solution of 1,4-anhydro-L-anhydro-L-threitol (2.45 g, 23.5 mmol ex Aldrich Chemical company) in a mixture of THF (75 ml) and $Et_2O$ (75 ml) at 0° C. was treated sequentially with triethylamine (7.2 ml, 51.7 mmol, 2.2 eq) and methanesulphonyl chloride (3.82 ml, 49.35 mmol, 2.1 eq). The mixture was stirred for 4 h then stored at 0° C. overnight (~16 h).

The reaction was filtered and the solids washed with THF (20 ml). The combined filtrate was evaporated in vacuo and partitioned between 10% aqueous citric acid (60 ml) and EtOAc (150 ml). The organic phase was dried ($MgSO_4$) and evaporated to afford (D4) as a colourless oil, 5.82 g (95%).

δ ($CDCl_3$) 3.12 (6H,s) 4.00 (2H,dd), 4.18 (2H,dd) and 5.25 (2H,dd).

Description 5

(S,S) trans 3,4-Diazidotetrahydrofuran (D5)

A mixture of the dimesylate (D4) (5.80 g, 22.3 mmol) and lithium azide (5.46, 111.5 mmol, 2.5 eq) in DMSO (60 ml) was heated at 100–110° C. for 40 h. After cooling to ambient the reaction was diluted with water (IL) and extracted with EtOAc (IL, 2×0.75 L). The combined organic phase was washed with water (0.5 L) and brine (0.5 L), dried over $MgSO_4$ and evaporated in vacuo to a pale yellow oil of the title compound, 2.18 g (61.5%).

δ ($CDCl_3$) 3.75 (2H,dd) and 3.90–4.05 (4H,m).

Description 6

(S,S) trans 3,4-Diaminotetrahydrofuran

To lithium aluminum hydride (2.05 g, 54 mmol) in dry THF (150 ml) at 0° C. was added the diazide (D5) (2.08 g, 13.5 mmol) in THF (50 ml) dropwise over 10 min. After 15 min the solution was allowed to warm to ambient, then stirred for 16 h.

The reaction mixture was re-cooled to 0° C. and quenched sequentially with $H_2O$ (2 ml), 15% aqueous NaOH (2 ml) and further $H_2O$ (6 ml) and warmed to ambient. After stirring for 1 h the mixture was filtered through celite, rinsed with THF (2×150 ml) and the combined filtrate evaporated in vacuo to afford (D6) as a pale yellow oil, 1.28 g (93%).

δ ($CDCl_3$) 1.30 (4H,bs), 3.20 (2H,dd), 3.50 (2H,dd) and 4.08 (2H,dd).

Description 7

(S,S) trans 3,4-bis(3-tert-Butyl-5-methylsalicylideamino)tetrahydrofuran (D7)

A solution of the (S,S)-diamine (D6) (1.26 g, 12.35 mmol) and 3-tert-butyl-5-methylsalicaldehyde (4.74 g, 24.70 mmol) in EtOH (75 ml) was heated at reflux for 3.5 h. The solution was cooled and solvent removed in vacuo to afford crude (5) as a yellow oil, 5.50 g (99%).

A sample of the crude material (4.55 g) was chromatographed on silica (Merck 9395, gradient of $CHCl_3$ in hexane) to afford pure (D7) as a yellow foam, 4.39 g (95.5% yield).

δ ($CDCl_3$) 1.42 (18H,s), 2.25 (6H,s), 3.95–4.10 (4H,m) 4.33 (2H,q), 6.90 (2H,d), 7.15 (2H,d), 8.30 (2H,s) and 13.15 (2H,bs).

Description 8

(2R,3R)-1,4-Dibenzyloxy-2,3-dimethanesulfonyloxybutane

To a solution of (2R,3R)-(+)-1,4-dibenzyloxy-2,3-butanediol (25.3 g, 83.7 mmol ex Aldrich Chemical Company) in dichloromethane (165 ml), cooled in an ice bath, was added methanesulfonyl chloride (13.0 ml, 167.4 mmol), followed by sol addition of triethylamine (23.3 ml, 167.4 mmol) such that the temperature did not rise above 5° C. Once the addition was complete the reaction was allowed to stir with ice-bath cooling for 3 hours. Water (600 ml) was then added and the organic phase separated. The aqueous phase was re-extracted with dichloromethane (200 ml) and the combined organic phases washed with water (400 ml) and brine (400 ml), dried (MgSO$_4$), and the solvent evaporated to afford a pale yellow solid. Trituration with diethyl ether afforded the title compound (28.2 g, 74%) as colourless crystals m.p. 72–73° C.

$^1$H n.m.r. (CDCl$_3$): δ 3.03 (s,6H,2×CH$_3$), 3.76 (m,4H,2×CH$_2$O),4.48 (d,2H,CH$_2$Ph), 4.57 (d,2H,CH$_2$Ph), 5.00 (m,2H,2×CH), 7.27–7.39 (m,10H,2×Ph)

$^{13}$C n.m.r. (CDCl$_3$): δ 38.8 (2×CH$_3$), 68.7 (2×CH$_2$) 73.7 (2×CH$_2$), 78.7 (2×CH), 128.1, 128.2, 128.6, 137.0 (2×Ph).

EI-MS:m/e 459 (MH$^+$), 367 (M$^+$-CH$_2$Ph). C$_{20}$H$_{26}$O$_8$S$_2$ requires: C: 52.39, H: 5.72%. found: C: 52.36, H: 5.59%.

Description 9

(2R,3R)-Dimethanesulfonyloxybutane-1,4-diol (2R,3R)-1,4-Dibenzyloxy-2,3-dimethanesulfonyloxybutane (27.6 g, 60.3 mmol) (D8) was dissolved in acetone (500 ml), a suspension of 10% Pd/C (29.9 g) in acetone (300 ml) added, and the mixture hydrogenated at 1 atm. pressure for 2 hours at ambient temperature. The mixture was then filtered three times through a pad of silica and Celite, and the solvent evaporated to give the title compound as a straw-coloured oil (14.7 g, 87%), which solidified on standing.

$^1$H n.m.r. (DMSO-d$_6$): δ 3.24 (s,6H, 2×CH$_3$), 3.69 (m,4H, 2×CH$_2$), 4.76 (m,2H,2×CH), 5.33 (t,2H,2×OH).

$^{13}$C n.m.r. (DMSO-d$_6$): δ 38.1 (2×CH$_3$), 59.7 (2×CH$_2$), 80.3 (2×CH).

EI-MS:m/e 279 (MH$^+$), 261 (MH$^+$-H$_2$O), 183 (M$^+$-OMs), 165 (M$^+$-OMs,H$_2$).

Description 10

(6R,7R)-Dimethanesulfonyloxy-2,4,9,11-tetraoxadodecane (2R,3R)-Dimethanesulfonyloxybutane-1,4-diol (14.7 g, 52.9 mmol) (D9) was dissolved in dimethoxymethane (89.5 ml) and dichloromethane (30 ml) at 40° C. Lithium bromide (0.91 g) and p-toluenesulfonic acid monohydrate (1.01 g, 5.29 mmol) were added, and the mixture heated under reflux for 3 hours. The reaction was allowed to cool to ambient temperature, and then poured into saturated sodium bicarbonate solution (200 ml), extracted with ethyl acetate (2×200 ml), dried (MgSO$_4$) and evaporated to give a colourless oil. This was purified by column chromatography on silica, eluting with 0–1% methanol in dichloromethane, to afford the title compound as a colourless oil (8.2 g, 42%).

$^1$H n.m.r. (CDCl$_3$); δ 3.13 (s,6H,2×CH$_3$), 3.39 (s,6H,2×OCH$_3$), 3.87 (m,4H,2×CH$_2$), 4.66 (m,4H,2×OCH$_2$O), 5.02 (m,2H,2×CH).

$^{13}$C n.m.r. (CDCl$_3$); δ 38.8 (2×SCH$_3$); 55.8 (2×OCH$_3$), 66.1 (2×CH$_2$), 78.4 (2×CH), 96.8 (2×OCH$_2$O)

CI-MS:m/e 384 (MNH$_4^-$). C$_{10}$H$_{22}$O$_{10}$S$_2$ requires C: 32.78, H: 6.05%.
found: C: 32.22, H: 5.62%.

Description 11

(5R,6R)-Dimethanesulfonyloxy-1,3-dioxepane

A solution of (6R,7R)-dimethanesulfonyloxy-2,4,9,11-tetraoxadodecane (8.2 g, 22.4 mmol) (D10) and p-toluenesulfonic acid monohydrate (0.2 g, 1.34 mmol) in toluene (165 ml) was heated under reflux overnight. The solvent was evaporated and the brown residue triturated with diethyl ether to afford the title compound as an off-white solid (5.9 g, 91%) m.p. 133–134° C.

$^1$H n.m.r. (CDCl$_3$): δ 3.13 (s,6H,2×CH$_3$), 3.84 (m,2H, CH$_2$), 4.06 (m,2H,CH$_2$), 4.77 (s,2H,OCH$_2$O), 4.81 (m,2H, 2×CH).

$^{13}$C n.m.r. (CDCl$_3$): δ 38.8 (2×CH$_3$), 64.1 (2×CH$_2$) 78.3 (2×CH), 94.6 (OCH$_2$O)

EI-MS:m/e 291 (MNH$^+$). 195 (M$^+$-OMs). C$_7$H$_{14}$O$_8$S$_2$ requires C: 28.96, H: 4.86%.
found: C: 29.22, H: 4.61%.

Description 12

(5R,6R)-Diazido-1,3-dioxepane

A mixture of (5R,6R)-dimethanesulfonyloxy-1,3-dioxepane (5.0 g, 17.2 mmol) D11 and lithium azide (42 g, 86 mmol) in dimethylsulphoxide (60 ml) was stirred and heated to 110–120° C. overnight. The reaction mixture was then cooled, poured into water (200 ml), and extracted with ethyl acetate (2×150 ml). The combined organic phases were washed with water (2×150 ml) and brine (150 ml), dried (MgSO$_4$) and evaporated to give the title compound as a brown oil (2.7 g, 85%).

$^1$H n.m.r. (CDCl$_3$): δ 3.49 (m,2H,2×CH), 3.74 (m,2H,2×CH$_2$), 3.93 (m,2H,CH$_2$), 4.73 (s,2H,OCH$_2$O).

$^{13}$C n.m.r. (CDCl$_3$): δ 64.3 (2×CH), 64.6 (2×CH$_2$) 94.3 (OCH$_2$O).

EI-MS:m/e 185 (MH$^+$), 157 (MH$^+$-N$_2$), 142 (M$^+$-N$_3$). C$_5$H$_8$N$_6$O$_2$ requires: C: 32.61, H: 4.38, N: 45.63%.
found: C: 32.33, H: 4.47, N: 45.38%.

Description 13

(5R,6R)-Diamino-1,3-dioxepane

To a slurry of lithium aluminium hydride (21.1 g, 55.3 mmol) in dry tetrahydrofuran (70 ml) at 0° C. under an argon atmosphere was added dropwise a solution of (5R,6R)-diazido-1,3-dioxepane (2.6 g, 14.1 mmol) (D12) in dry tetrahydrofuran (50 ml). During the addition the reaction temperature was maintained below 10° C. with an ice-salt bath. One completion, the reaction mixture was allowed to warm to ambient temperature, and stirred for a further 1.5 hours. It was then re-cooled and the reaction quenched by addition of water (2 ml), 2M, NaOH (2 ml), and water (4 ml), the temperature again being maintained below 10° C. by means of an ice-salt bath. The quenched reaction mixture was allowed to warm to ambient temperature, stirred for a further 2 hours, then filtered through Celite, and the filter pad washed well with tetrahydrofuran. The combined filtrates were evaporated to afford the title compound as a pale yellow oil (1.3 g, 70%).

¹H n.m.r. (CDCl₃): δ 1.56 (brs,4H,2×NH₃), 2.62 (m,2H, 2×CH), 3.58 (m,2H,CH₂), 3.77 (m,2H,2×CH₂), 4.72 (s,2H, OCH₂O)

¹³C n.m.r. (CDCl₃): δ 57.9 (2×CH), 67.5 (2×CH₂) 93.8 (OCH₂O). C₅H₁₂N₂O₂ requires: C: 45.44, H: 9.15, N: 21.20%.

found: C: 45.13, H: 8.76, N: 19.58%.

EI-MS:m/e 133 (MH⁺), 116 (M⁺-NH₂)⁺.

Description 14

Preparation of (5R,6R)-Di-(3,5-di-tert-butyl) salicylideamino-1,3-dioxepane (5R,6R)-Diamino-1,3-dioxepane (1.0 g, 7.6 mmol) (D13) and 3,5-di-tert-butylsalicaldehyde (3.6 g, 15.4 mmol, 2 eq.) were dissolved in ethanol (100 ml), and the solution stirred under reflux for 3 hours. The reaction mixture was then allowed to cool, the solvent was evaporated, and the residue purified by column chromatography on silica, eluting with 4% diethyl ether in hexane. This afforded the title compound as a bright yellow foam (3.5 g, 82%).

¹H n.m.r. (CDCl₃): δ 1.23 (s,18H,6×CH₃), 1.41 (s,18H, 6×CH₃), 3.85 (m,2H,CH₂), 4.07 (m,2H,CH₂), 4.87 (s,2H, OCH₂), 6.99 (d,2H,Ar), 7.33 (d,2H,Ar), 8.33 (s,2H,2× CH=N), 13.20 (brs,2H,2×OH).

¹³C n.m.r. (CDCl₃): δ 29.4 (6×CH₃), 31.4 (6×CH₃) 34.1 (2×CCH₃), 35.0 (2×CCH₃), 67.7 (2×CH), 73.8 (2×CH₂), 94.2 (OCH₂O), 117.6, 126.4, 127.4, 136.6, 140.3, 157.9 (Ar), 168.4 (2×C=N) C₃₅H₅₂N₂O₄ requires: C: 74.43, H: 9.28, N: 4.96%.

found: C: 74.56, H: 9.15, N: 4.92%.

CI-MS:m/e 565 (MH⁺).

Description 15

(3R,4R)-Diacetoxytetrahydropyran (D15)

A solution of 3,4-di-O-acetyl-D-Xylal² (11.16 g) in 50% aqueous ethanol (400 ml) containing PtO₂ (400 mg) was hydrogenated at atmospheric pressure for 3.5 hours at 25° C. The suspension was filtered through celite, washed with 50% aqueous ethanol (50 ml) and water (50 ml), and the combined filtrate evaporated in vacuo to afford the title compound as a colourless oil, 9.6 g (85%).

δ (CDCl₃): 1.30–1.50 (1H,m), 2.10 (6H,S), 2.10–2.20 (1H,m), 3.35–3.60 (2H,m), 3.80–4.00 (2H,m) and 4.80–5.00 (2H,m).

2. Dictionary of Organic Compounds, 5th Edition, 1982, Chapman & Hall, London, 579 and references therein.

Description 16

(3R,4R)-Dimethanesulfonyloxytetrahydropyan (D16)

Sodium (∼50 mg) was dissolved in methanol (100 ml) at ambient. To the resulting solution was added a solution of the diester (D15) (9.56 g), 47.3 mmol) in methanol (100 ml) and the mixture stirred for 72 hours. Amberlite IR 120H⁺ resin (20 g) was added and the mixture filtered. Concentration of the filtrate in vacuo afforded the diol as a colourless oil. This was dissolved in a mixture of tetrahydrofuran (220 ml) and diethyl ether (220 ml). Triethylamine (10.86 g, 107.5 mmol) was added and the solution cooled to 0° C. Methanesulphonyl chloride (11.76 g, 102.7 mmol) was added dropwise at 0° C., the solution was stirred for a further hour then stored at 4° C. for 16 hours. The resulting suspension was filtered and the solids washed with tetrahydrofuran (2×95 ml) and diethyl ether (2×180 ml). The combined filtrate was evaporated in vacuo and the residue partitioned between ethyl acetate (200 ml) and 10% aqueous citric acid (200 ml). The organic phase was dried (MgSO₄), filtered and concentrated in vacuo to a colourless foam to afford the title compound, 12.07 g (93%).

δ (CDCl₃): 3.10 (6H,s), 2.00–2.40 (2H,m), 3.40–4.20 (4H,m), 4.55–4.65 (1H,m) and 4.70–4.85 (1H,m).

Description 17

(3R,4S)-Diaminotetrahydropyran (D17)

The dimesylate (D16(12.07 g, 44 mmol) was dissolved in dimethylsulphoxide (88 ml) and treated with lithium azide (10.8 g, 220 mmol). The mixture was heated at 100° C. for 40 hours, then cooled to ambient and poured into water (1.03 L) and extracted with ethyl acetate (1.03 L, 2×0.59 L). The combined organic phase was washed with water (300 ml) and brine (300 ml), dried over MgSO₄ and concentrated in vacuo to give the crude diazide as a brown oil, 3.7 g. This was dissolved in tetrahydrofuran (45 ml), and added dropwise to a cold (0° C.) suspension of lithium aluminium hydride (3.34 g, 88 mmol) in tetrahydrofuran (220 ml), maintaining the temperature below +10° C. After completion of addition the suspension was stirred at 0° C. for 0.5 hours then warmed to ambient and stirred for 16 hours.

The mixture was recooled to 0° C. and quenched sequentially with water (3.34 ml) in tetrahydrofuran (5 ml), 15% aqueous sodium hydroxide (3.34 ml) and further water (10 ml). The mixture was allowed to warm to ambient, stirred for one hour then filtered through celite, rinsing with tetrahydrofuran (2×400 ml). The combined filtrate was concentrated in vacuo to give the title diamine as a colourless oil, 2.62 g (51%).

δ (CDCl₃); 1.20–1.90 (6H,m), 2.40–2.50 (2H,m), 2.90–3.40 (2H,m) and 3.80–4.00 (2H,m).

Description 18

(3R,4S)-bis-(3,5-Di-tert-Butylsalicylideamino) tetrahydropyran, (D18)

To the diamine (D17) (2.55 g, 22 mmol) in ethanol (220 ml) was added 3,5-di-tert-butylsalicaldehyde (10.3 g, 44 mmol). The mixture was heated at reflux for 2 hours, cooled to ambient filtered, and the crystalline product dried in vacuo to afford the title compound as yellow crystals, 4.81 g, (40%).

δ (CDCl₃): 1.20 (18H,s), 1.40 (18H,s), 1.50–2.20 (2H,m), 3.50–3.70 (4H,m), 4.00–4.15 (2H,m), 7.00 (2H,s), 7.35 (2H,bs), 8.33 (1H,s), 8.37 (1H,s) and 13.20 (2H,bs).

Description 19

(3R,4S)-bis (3-tert-Butyl-5-methylsalicylideamino) tetrahydropyran (D19)

A solution of the diamine (D17) (0.62 g, 5.35 mmol) and 3-tert-butyl-5-methylsalicaldehyde (2.05 g, 10.7 mmol) in ethanol (40 ml) was heated at reflux for 2 hours. The solution was cooled then stored at 4° C. for 70 hours to afford a yellow precipitate. This was filtered, washed with cold 95% aqueous ethanol (5 ml) and dried in vacuo to afford the title compound, 1.22 g (49%).

δ (CDCl₃): 1.40 (18H,s), 1.80–2.20 (2H,m), 2.20 (6H,s), 3.40–3.70 (4H,m), 4.00–4.20 (2H,m), 6.80 (2H,bs), 7.05 (2H,bs), 8.27 (1H,s), 8.30 (1H,s) and 13.30 (2H,bs).

Description 20

(3S,4S)-bis (3,5-di-tert-Butylsalicylideamino) tetrahydrofuran (D20)

A solution of (S,S)-diamine (D6) (0.96 g, 9.4 mmol) and 3,5-di-tert-butylsalicaldehyde (4.4 g, 18.8 mmol) in ethanol (90 ml) was heated at reflux for 2 hours. The mixture was cooled to 0° C., filtered and the solids washed with cold ethanol and dried to afford the title compound as yellow crystals, 3.07 g (61%).

δ (CDCl$_3$): 1.27 (18H,s), 1.45 (18H,s), 3.95–4.10 (4H,m), 4.30–4.40 (2H,m), 7.05 (2H,d), 7.40 (2H,d), 8.35 (2H,s) and 13.20 (2H,s).

Description 21

(3S,4R)-Dihydroxy-(2R)-(hydroxymethyl) tetrahydropyran (D21)

A solution of D-Glucal[3] (16.0 g, 0.11 mole) in 50 % aqueous ethanol (500 ml) was treated with platinum oxide (0.75 g) and hydrogenated at ambient at atmospheric pressure for 5 hours. The suspension was treated with charcoal (50 g) filtered through celite (200 g) and the solids washed with 50% aqueous ethanol (300 ml). The combined filtered was evaporated in vacuo and dried over P$_2$O$_5$ to afford the title compound as a colourless oil, 16.0 g (99%).

δ(CD$_3$OD): 1.50–1.70 (1H, m), 180–2.20 (1H, m), 3.00–3.20 (2H, m), 3.30–3.70 (3H, m), 3.80–4.00 (2H, m) and 4.90 (3H, bs)

3. Dictionary or Organic Compounds, 5th Edition, 1982, Chapman and Hall, London, 2754, and references therein.

Description 22

(3S, 4R)-Dihydroxy-(2R)-(triphenylmethoxymethyl) tetrahydropyran (D22)

A solution of the triol (D21) (1.76 g, 11.9 mmol) in pyridine (20 ml) was treated with trityl chloride (3.31 g, 11.9 mmol) and 4-(dimethylamino)pyridine (50 mg). Diisopropylethylamine (1.92 g, 14.8 mmol, 1.25 eq) was added and the solution stirred for 4 hours at ambient temperature.

The mixture was poured into water (200 ml) and extracted with diethyl ether (2×200 ml). The combined organic phase was washed with 10% aqueous citric acid (100 ml) and brine (100 ml), dried over MgSO$_4$ and concentrated in vacuo to an oil. The residue was chromatographed on silica (eluent:gradient of methanol in chloroform) to afford the title compound as a colourless foam, 3.70 g (79.7%)

δ(CDCl$_3$): 160–1.80 (1H, m), 1.90–2.00 (1H, m), 2.70 (2H, bs, D$_2$O exch), 3.25–3.50 (5H, m), 3.60–3.70 (1H, m), 3.90–4.00 (1H, m) and 7.20–7.50 (15H, m).

Description 23

(3R, 4R)-Dimethanesulphonyloxy-(2R)- (triphenylmethoxymethyl)tetrahydropyran (D23)

To the diol (D22) (3.10 g, 7.95 mmol) in a mixture of diethyl ether and tetrahydrofuran (2:1, 150 ml) was added triethylamine (1.76 g, 17.5 mmol). The mixture was cooled to 0° C. and methanesulphonyl chloride (1.91 g, 16.7 mmol) added. After 2 hours the suspension was filtered and the filtrate concentrated in vacuo, then redissolved in ethyl acetate (200 ml). The solution was washed with 10% aqueous citric acid (100 ml) and brine (50 ml), then dried over MgSo$_4$. Solvent was removed in vacuo and the residue dried to afford (12) as a colourless solid, 4.26 g (95%).

δ(CDCl$_3$): 2.20–2.50 (2H, m), 2.50 (3H, s), 3.10 (3H, s), 3.20–3.30 (1H, m), 3.40–3.60 (3H, m), 3.95–4.10 (1H, m), 4.70–4.80 (2H, m) and 7.20–7.50 (15H, m).

Description 24

(3R, 4S)-bis(3,5-Di-tert-butylsalicylideamino)-(2S)- (triphenylmethoxymethyl)tetrahydropyran (D24)

A mixture of the dimesylate (D23) (2.85 g, 5.22 mmol) and lithium azide (1.28 g, 26.1 mmol) in dimethyl sulphoxide (20 ml) was heated at 100–110° C. for 24 hour. The solution was cooled, poured into water (200 ml) and extracted with ethyl acetate (2×300 ml). The combined organic phase was washed with water (2×300 ml) and brined (300 ml), and dried over MgSo$_4$. Removal of the solvent afforded the intermediate diazide as a yellow foam (1.52 g).

A 1.40 g portion of the diazide in tetrahydrofuran (10 ml) was added to a suspension of lithium aluminium hydride (4.70 mg, 12.4 mmol) in tetrahydrofuran (30 ml) at 0° C. After stirring at 0° C. for 1 hour the mixture was allowed to warm to ambient and stirred for 16 hours. The suspension was recooled to 0° C. and quenched sequentially with water (0.5 ml), 15% aqueous sodium hydroxide (0.5 ml) and further water (1.5 ml). After warming the ambient and stirring for 1 hour the mixture was filtered, the solids washed with tetrahydrofuran (2×20 ml) and the combined filtrate evaporated to afford the crude diamine as a foam (1.28 g).

A portion of the diamine (1.18 g) and 3.5-di-tert-butylsalicaldehyde (1.42 g, 6.08 mmol) in ethanol (30 ml) was heated at reflux for 4 hour then cooled to ambient. Solvent was removed in vacuo and the residue chromatographed on silica (eluent: gradient of chloroform in hexane) to afford the title compound as a yellow powder, 210 mg, in 8.4% overall yield from (D23).

δ(CDCl$_3$): 1.25 (9H, m), 1.30–1.60 (2H, m), 1.32 (9H, s) 1.40 (9H, s), 1.50 (9H, s), 2.40–2.55 (1H, s), 2.70–2.80 (1H, s), 3.30–3.60 (2H, m), 3.90–4.30 (3H, m), 6.85 (1H, bs), 7.00–7.35 (16H, m), 7.38 (1, bs), 7.45 (1H, bs), 8.30 (1H, s), 8.50 (1H, s), 13.25 (1H, s) and 13.50 (1H, s).

Description 25

(±)trans-1-Benzoyl-3,4-bis(methanesulphonyloxy) piperidine (D25)

(±)trans-1-Benzoylpiperidine-3,4-diol[4] (3 g, 13.6 mmol) was suspended in dichloromethane (70 ml) and triethylamine (5.74 ml, 43 mmol) was added. The mixture was cooled to −10° C. and methanesulphonyl chloride (2.6 ml, 34 mmol) added over 5 min. After a further 15 min the mixture was poured into ice-water (50 ml) and the organic layer washed with 5% aqueous citric acid (30 ml). The solution was dried over MgSO$_4$ and concentrated in vacuo to a foam, 5.3 g (100%).

δ$_H$ (CDCl$_3$):1.95 (2H, m), 2.30 (2H, m), 3.15 (6H, s), 4.70 (2H, m), 4.85 (2H, m) and 7.45 (5H, m).

4. V. Petrow and O. Stephenson, *J. Pharm. Pharmacol,* 1962, 14, 306–314.

Description 26

(±)trans-1-Benzoyl-3,4-diazidopiperidine (D26)

A mixture of the dimesylate (D25) (5.3 g, 14 mmol) and lithium azide (3.4 g, 69 mmol) in dimethylsulphoxide (36 ml) was heated at 100° C. for 18 hours. After cooling the reaction mixture was partitioned between dichloromethane (200 ml) and water (50 ml). The aqueous phase was separated and further extracted with dichloromethane (100 ml), 50 ml) and the combined organic extracts washed with water (3×50 ml), dried (Na$_2$SO$_4$) and concentrated in vacuo. The residue was chromatographed on silica (eluent: gradient of methanol in dichloromethane) to afford the title compound as a colourless solid, 900 mg (24%).

δ$_H$ (CDCl$_3$): 1.60 (2H, m), 2.10 (2H, m), 3.05 (2H, m), 3.20 (2H, m) and 7.40 (5H, m).

Description 27

(±)trans-1-Benzoyl-3,4-diaminopiperidine (D27)

A solution of the diazide (D26) (450 mg, 1.7 mmol) in ethanol (30 ml) was treated with Lindlar catalyst (5%

Pd/CaCO$_3$, 250 mg) and stirred under hydrogen (1 atm) for 24 hour. The mixture was filtered and solvent removed in vacuo to afford the title compound as oil, 350 mg (94%).

$\delta_H$ (DMSO): 1.20 (1H, m), 1.65–1.80 (2H, m), 2.20 (2H, m), 2.70 (2H, ), 3.00 (1H, m), 3.30 (1H, m), 4.40 (1H, m) and 7.40 (5H, m).

Description 28

(−)trans-1-Benzoyl-3,4-bis(3.5-di-tert-butylsalicylideamino)piperidine (D28)

A solution of the amine (D27) (350 mg, 1.6 mmol) and 3,5-di-tert-butylsalicaldehyde (960 mg, 4.1 mmol) in ethanol (40 ml) was heated at reflux for 3 hours. The mixture was cooled and filtered to afford the racemic bis-imine, 652 mg (63%).

A 100 mg sample was separated by chiral hplc (CHIRALPAK AD, eluent 2% ethanol in hexane) to afford the title compound as a single enantiomer, $[\alpha]^{25}_D = -228°$ (c=0.13, CHCl$_3$).

$\delta_H$ (CDCl$_3$): 1.20 (18H, s), 1.45 (18H, s), 2.00 (2H, m), 3.25 (2H, m), 3.45 (1H, m), 3.55 (1H, m), 4.35 (2H, m), 6.95 (2H, s), 7.40 (7H, m), 8.30 (2H, s) and 13.15 (2H, bs).

Description 29

(±) 3,4-bis (3-tert-Butyl-5-methylsalicylideamino) tetrahydrofuran manganese (III) chloride (D29)

A suspension of the racemic ligand (D3) (690 mg, 1.53 mmol) in EtOH (25 ml) was heated with Mn(OAc)$_2$·4H$_2$O (750 mg, 3.06 mmol) at reflux for 18 h. LiCl (195 mg, 4.49 mmol) was added and reflux continued for a further 0.5 h. Solvent was removed in vacuo and the residue chromatographed on silica (Merck 9385, 100 g) eluting with a gradient of MeOH in CHCl$_3$, to afford the title compound as a brown powder (90 mg, 11%) together with unreacted (D3), 420 mg (61% recovery).

Description 30

(S,S) trans 3,4-bis (3-tert-Butyl-5-methylsalicylideamino)tetrahydrofuran manganese (III) chloride (D30)

Method A (using manganese (II) acetate)

A solution of (D7) (0.95 g, 2.11 mmol) and Mn(OAc)$_2$·4H$_2$O (1.03 g, 4.22 mmol) in EtOH (40ml) was heated at reflux for 17 h. Lithium chloride (268 mg, 6.33 mmol) was added and reflux continued for a further 0.5 h. After cooling to ambient the solvent was removed in vacuo and the residue chromatographed on silica (Merck 9385, gradient of MeOH in CHCl$_3$) to afford (E3) as a brown powder, 26 mg (2.3%), together with unreacted (D7), 683 mg (72%).

Method B (using manganese (III) acetate)[5].

A solution of (D7) (1.53 g, 3.4 mmol) in a mixture of CH$_2$Cl$_2$ (17 ml) and MeOH (17 ml) was treated with Mn(OAc)$_3$·2H$_2$O (0.01 g, 3.4 mmol). The mixture was heated at reflux for 3 h, cooled to ambient and treated with lithium chloride (0.21 g, 5.1 mmol). After stirring for 16 h the solvent was reduced in vacuo to ca. 8 ml, Et$_2$O (70 ml) was added and the suspension stirred for 1 h. The mixture was filtered and the solids washed with Et$_2$O (3×20 ml) and dried in vacuo to afford (E3) as a brown powder, 1.57 g (86%).

5 T. Matsushita and T. Shono. *Bull. Chem. Soc. Japan*, 1981, 54, 3743–3748.

Description 31

Preparation of (R,R)-5,6-bis-(3,5-di-tert-butylsalicylideamino)-1,3-dioxepane]mangenese (III) chloride (D31)

(5R, 6R)-Di-(3,5-di-tert-butyl)salicylideamino-1,3-dioxepane (1.0 g, 1.77 mmol) (D14) and manganese (II) acetate tetrahydrate (2.17 g, 8.87 mmol) were suspended in 95% ethanol (50 ml), and the mixture stirred under reflux overnight. Lithium chloride (0.38 g, 8.96 mmol) was then added and heating continued for a further 30 minutes. The reaction mixture was then cooled, water (60 ml) added, and filtered through Celite. The dark precipitate was washed well with water, then dissolved in dichloromethane (80 ml), dried (MgSO$_4$), and the solvent evaporated to give the title compound as a dark brown solid (0.9 g, 78%).

C$_{35}$H$_{50}$N$_2$O$_4$MnCl requires C:64.36, H:7.72, N:4.29%. found: C:64.57, H:7.57, N:4.09% CI-MS: m/e 565 (MH-Mn, Cl)$^+$, 235 (3,5-di-tert-butylsalicaldehydeH)$^+$.

Description 32

(3R,4S)-bis-(3,5-di-tert-butylsalicylideamino) tetrahydropyran-manganese (III) chloride (D32)

A solution of the ligand (D18) (4.81 g, 8.8 mmol) in dichloromethane-methanol (1:1, 88 ml) was treated with manganese triacetate dihydrate (2.35 g, 8.8 mmol) and the mixture heated at reflux for 4 hours. Lithium chloride (0.56 g, 13.2 mmol) was added and heating at reflux continued for a further 1 hour. The mixture was cooled, concentrated in vacuo and the residue triturated with diethyl ether (220 ml). The solid product was filtered, washed with diethyl ether (2×65 ml) and dried to afford (5) as a brown powder, 5.3 g (94%).

Description 33

(3R, 4S)-bis-(3-tert-butyl-5-methylsalicylideamino) tetrahydropyran-manganese (III) chloride (D33)

A solution of the ligand (D19) (928 mg, 2 mmol) in dichloromethane-methanol (1:1, 20 ml) was treated with manganese triacetate dihydrate (536 mg, 2 mmol) and heated at reflux for 3 hours. The mixture was cooled to ambient, lithium chloride (128 mg, 3 mmol) was added and the solution stirred for 1 hour. The reaction mixture was concentrated in vacuo and the residue triturated with diethyl ether (40 ml). The solid product was filtered, washed with diethyl ether (2×15 ml) and dried in vacuo to afford the title compound as a brown powder, 1.09 g (98%).

Description 34

(3S,4S)-bis-(3,5-di-tert-Butylsalicylideamino) tetrahydrofuran-manganese (III) chloride (D34)

A solution of the ligand (D20) (1.07 g, 2 mmol) and manganese triacetate dihydrate (536 mg, 2 mmol) in a mixture of dichloromethane and methanol (1:1, 20 ml) was heated at reflux for 6.5 hour. The solution was cooled to ambient, lithium chloride (128 mg, 3 mmol) was added and the mixture stirred for 16 hours. The reaction mixture was concentrated in vacuo and the residue triturated with diethyl ether (50 ml). The solid product was filtered, washed with diethyl ether (2×15 ml) and dried in vacuo to afford the title compound as a brown powder, 1.12 g (89%).

Description 35

(3R, 4S)-bis-(3.5-Di-tert-Butylsalicylideamino)-(2R)-(triphenylmethoxymethyl)tetrahydropyran-manganese (III) chloride (D35)

To the ligand (D24) (160 mg, 195 mmol) in dichloromethane-methanol (3:2, 5 ml) was added NaOH (0.93 ml of 0.417 molar in methanol, 390 mmol) and manganese triacetate dihydrate (52.5 mg, 195 mmol). The solution was heated at reflux for 3 hours, lithium chloride (12.5 mg, 300 mmol) added and the mixture stirred for 15 hours.

Solvent was removed in vacuo and the residue triturated with diethyl ether (10 ml). The solid product was filtered, washed with diethyl ether (2×2 ml) and dried with afford the title compound as a brown powder, 136 mg (77%).

Description 36

(−)trans-1-Benzoyl-3,4-bis(3,5-di-tertbutylsalicylideamino) piperidine-manganese (III) chloride (D36)

A mixture of the (−) ligand (D28) (20 mg, 0.013 mmol) and manganese triacetate dihydrate (10 mg, 0.037 mmol) in dichloromethane-methanol (3:2, 5 ml) was heated at reflux for 4 hour. Lithium chloride (1.6 mg, 0.038 mmol) was added and reflux continued for a further 1 hour.

Solvent was removed in vacuo and the residue chromatographed on silica (eluent: 10% methanol in dichloromethane) to afford the title compound as a brown powder, 22 mg (97%).

Descriptions of Intermediates for the Preparation of Compounds of Formula (III)

Description 37:

(R)-1-Phenyl-1,2-bis(3-tert-butyl-5-methylsalicylideamino)ethane (D37)

(R)-1,2-Diamino-1-phenylethane (prepared from (R)-2-aminophenylacetamide[6] via reduction to the diamine by the method of Brown and Heim[7]) (1.36 g, 10.0 mmol) was dissolved in ethanol (50 ml) and solid 2-hydroxy-3-tert-butyl-5-methylbenzaldehyde (prepared from 2-tert-butyl-4-methyl-phenol by the method of Casiraghi et al[8]) (3.84 g, 20.0 mmol) was added. After a 90 min at reflux the reaction was cooled and water (1 ml) was added. The yellow solid formed was removed by filtration, washed with 95% aqueous ethanol (10 ml) and dried in vacuo over $P_2O_5$ to give the title compound as yellow solid. 3.33 g, 69% yield.

$\delta(CDCl_3)$ 1.41 (9H,s), 1.43 (9H, s), 2.22 (3H, s), 2.23 (3H, s), 3.93 (1H, dd), 4.12 (1H, dd), 4.68 (1H, dd), 6.84 (2H, d), 7.09 (2H, s), 7.30–7.50 (5H, m), 8.25 (1H, s), 8.37 (1H, s), and 13.50 (2H, bs).

6. C. G. Nielson and D. F. Ewing, *J. Chem. Soc.* (C), 1966, pp 393–397,

7. H. C. Brown and P. Heim, *J. Org. Chem.*, 1973, 38, p.p. 912–916.

Description 38:

(R)-1-Phenyl-1,2-bis(3.5-di-tert-butyl-salicylideamino)ethane (D38)

(R)-1,2-Diamino-1-phenylethane (0.68 g, 5.0 mmol) was dissolved in ethanol (50 ml) and 2-hydroxy-3,5-di-tert-butyl-benzaldehyde (prepared from 2,4-di-tert-butylphenol by the method of Casiraghi et al[8]) (2.34 g, 10.0 mmol) was added. The reaction was refluxed for 2 hours, cooled to room temperature and water (1 ml) was added to the stirring solution. The product was isolated by filtration, washed with 95% aqueous ethanol (5 ml) and dried in vacuo over $P_2O_5$ to give the title compound as yellow solid, 2.11 g, 74% yield.

$\delta(CDCl_3)$ 1.24 (9H, s), 1.27 (9H, s), 1.41 (9H, s), 1.45 (9H, s), 3.95 (1H, dd), 4.15 (1H, dd), 4.70 (1H, dd), 7.05 (2H, bs), 7.30–7.50 (7H, m), 8.34 (1H, S), 8.42 (1H, s), and 13.60 (2H, bs).

8. G. Casiraghi, G. Casnati, G. Puglia, G. Sartori and G. Terenghi, *J. Chem. Soc. Perkin T.* 1980, p.p. 1862–1865.

Description 39:

(S)-1-Methyl-1,2-bis(3-tert-butyl-5-methylsalicylideamino)ethane (D39).

A suspension of (S)-1,2-diaminopropane dihydrochloride (290 mg, 2 mmol) in EtOH (5ml) was treated with 1M ethanolic NaOH (4ml, 4 mmol). 2-Hydroxy-5-tert-butyl-3-methylbenzaldehyde (770 mg, 4 mmol) was added and the mixture heated at reflux for 1.5 H. The suspension was filtered, partially evaporated and a small quantity of water added to precipitate the title compound as yellow solid. This was filtered, washed with 95% aqueous EtOh and dried in vacuo over $P_2O_5$, to afford the title compound 730 mg (86% yield).

$\delta(CDCl_3)$, 1.33 (3H, s), 1.36 (18H, d), 2.25 (6H, s), 3.62 (2H, m), 3.76 (1H, m), 6.80 (2H,s), 7.03 (2H, s), 8.20 (1H, s), 8.25 (1H, s), 13.50 (2H, bs)

Description 40:

(S)-1-Isopropyl-1,2-bis(3-tert-butyl-5-methylsalicylideamino) ethane (D40).

To sodium borohydride (1.13 g, 30 mmol) in glyme (30 ml) under nitrogen was added (S)-Valinamide hydrochloride (1.53 g, 10 mmol) suspended in glyme (35 ml) with stirring. The solution was cooled to 10° C. and boron trifluoride etherate (4.9 ml, 40 mmol) in glyme (10 ml) was added dropwise over 20 min, then the mixture was heated at reflux for 16 h. After cooling to ambient water (7.5 ml), followed by 3M NaOH (15 ml), was added and the resulting clear solution refluxed for 2 h. Solvent was removed in vacuo to afford a white solid which was extracted with chloroform (3×10 ml), the combined extract being evaporated to afford the diamine (0.34 g). This was dissolved in ethanol (15 ml) and treated with 2-hydroxy-3-tert-butyl-5-methyl benzaldehyde (1.28 g, 6.6 mmol). The solution was heated at reflux for 2 h, cooled, concentrated in vacuo and the residue chromatographed on silica (Merck 9385, eluting with 0–6% MeOH in chloroform) to afford the title compound, 0.73 g (16% yield).

$\delta(CDCl_3)$, 1.04 (6H, m), 1.39 (18H, 2s), 2.10 (1H, m), 2.24 (6H, s), 3.3–4.0 (3H, bm), 6.85 (2H, m), 7.09 (2H, m), 8.24 (2H, s), 13.60 (2H, bs).

What is claimed is:

1. A compound of formula (III):

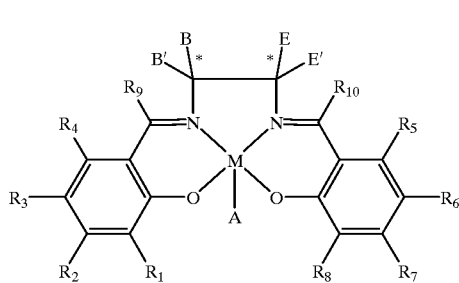

(III)

in which M is a transition metal ion;
A is a counter-ion if required;
B, B', E and E' are independently selected from the group consisting of hydrogen aryl, $C_{1-5}$ alkyl, silyl or aryl-$C_{1-6}$ alkyl in which any aryl or alkyl moiety is optionally substituted or B' and B or E' and E together form a $C_{2-6}$ polymethylene link; with the proviso that only one of the carbons marked with an asterisk is a chiral center; $R_1$, $R_2R_3$, $R_4R_5$, $R_6$, $R_7$, $R_8$, $R_9$ and $R_{10}$ are independently hydrogen, alkyl or alkoxy.

2. A compound according to claim 1, wherein, $R_2$, $R_4$, $R_5$ and $R_7$ each independently represent hydrogen and $R_1$, $R_3$, $R_6$ and $R_8$ each independently represent $C_{1-6}$ alkyl.

3. A compound according to claim 1 or claim 2, wherein, one of B and E is phenyl, methyl or isopropyl and the other is hydrogen.

4. A compound according to claim 1 selected from the list consisting of:
(R)-1-phenyl-1,2-bis(3-tert-butyl-5-methylsalicylideamino)ethane-manganese (III) chloride;
(R)-1-phenyl-1,2-bis(3,5-di-tert-butyl-salicylideamino)ethane-manganese (III) chloride; and
(S)-1-isopropyl-1,2-bis(3-tert-butyl-5-methylsalicyclideamino) ethane-manganese (III) chloride.

5. A process for the preparation of compounds of formula (III) of claim 1 which comprises:
(A) forming a transition metal complex of the following compound of formula (IV):

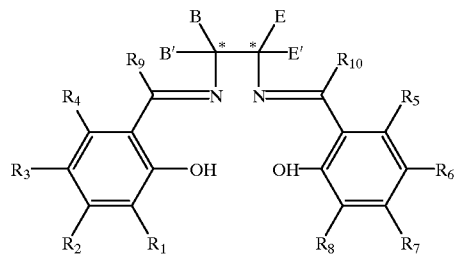

(IV)

where variables $R_1$, $R_2$, $R_3$, $R_4$, $R_5$, $R_6$, $R_7$, $R_8$, $R_9$ and $R_{10}$, B, B', E and E' are as defined in relation to formula (III), and thereafter if necessary separating any enantiomers;

(b) first forming a compound of formula (IV) by condensing sequentially, in any order, a compound of formula (V):

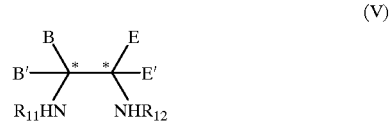

(V)

where B, B', E and E' are as defined in formula (III) and $R_{11}$ and $R_{12}$ independently represent hydrogen or an amine protecting group, providing at least one of $R_{11}$ and $R_{12}$ is hydrogen, with:

(i) a compound of formula (VI);

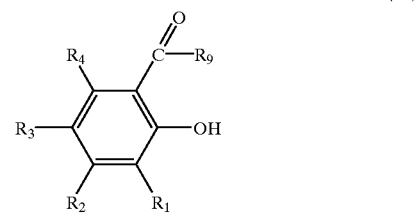

(VI)

wherein $R_1$, $R_2$, $R_3$, $R_4$ and $R_9$ are as defined in relation to formula (III); and (ii) a compound of formula (VII),

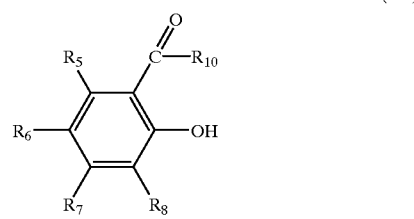

(VII)

wherein $R_5$, $R_6$, $R_7$, $R_8$ and $R_{10}$ are as defined in relation to formula (III); and thereafter as required removing any protecting group $R_{11}$ and $R_{12}$, isolating the required compound including if necessary separating any enantiomers; and thereafter forming the transition metal complex as described in reaction (a) above.

6. An intermediate compound of formula (IV) of claim 5.

* * * * *